(12) United States Patent
Harada et al.

(10) Patent No.: US 11,484,186 B2
(45) Date of Patent: Nov. 1, 2022

(54) ENDOSCOPE

(71) Applicant: FUJIFILM Corporation, Tokyo (JP)

(72) Inventors: Takashi Harada, Kanagawa (JP);
Shozo Iyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 406 days.

(21) Appl. No.: 16/744,187

(22) Filed: Jan. 16, 2020

(65) Prior Publication Data

US 2020/0146531 A1    May 14, 2020

Related U.S. Application Data

(63) Continuation of application No. PCT/JP2018/022359, filed on Jun. 12, 2018.

(30) Foreign Application Priority Data

Jul. 18, 2017    (JP) .............................. JP2017-139137

(51) Int. Cl.
*A61B 1/00*    (2006.01)
(52) U.S. Cl.
CPC ...... *A61B 1/00087* (2013.01); *A61B 1/00002* (2013.01); *A61B 1/00133* (2013.01)
(58) Field of Classification Search
None
See application file for complete search history.

(56) References Cited

U.S. PATENT DOCUMENTS 5,460,168 A    10/1995 Masubuchi et al.
5,562,600 A    10/1996 Matsuno
(Continued)

FOREIGN PATENT DOCUMENTS

CN    104665753    6/2015
CN    105982636    10/2016
(Continued)

OTHER PUBLICATIONS

"Office Action of Japan Counterpart Application" with English translation thereof, dated Sep. 10, 2021, p. 1-p. 9.
(Continued)

*Primary Examiner* — Timothy J Neal
(74) *Attorney, Agent, or Firm* — JCIPRNET

(57) ABSTRACT

An endoscope in which an erecting operation mechanism is provided at an operation section and that can prevent an increase in size of a holding part of the operation section is provided. An endoscope according to the present invention includes an operation section 22 having an operation section main body 32, a holding part 34 connected to the operation section main body 32, and an extension part 36 extending from the holding part 34 toward a distal end side; an insertion section 24 provided on a distal end side of the extension part 36; an erecting base 30 provided at a distal end part 26 of the insertion section 24; a movable member 96 that is provided at the extension part 36 and that moves in association with an operation of an erecting operation lever 20; a wire 60 that is coupled to the erecting base 30 at a distal end side thereof, that is coupled to the movable member 96 at a proximal end side thereof, and that is pushed/pulled by the movable member 96; and an attachment member 98 that is provided at a proximal end of the wire 60 and that is engaged with the movable member 96 in an attachable/detachable manner by a one-touch operation.

13 Claims, 28 Drawing Sheets

(56) References Cited

U.S. PATENT DOCUMENTS

| 5,569,157 | A | 10/1996 | Nakazawa et al. |
| 5,707,344 | A | 1/1998 | Nakazawa et al. |
| 10,165,930 | B2 | 1/2019 | Tanaka et al. |
| 10,357,145 | B2 | 7/2019 | Fukushima et al. |
| 2005/0192475 | A1 | 9/2005 | Okada |
| 2018/0092512 | A1 | 4/2018 | Hiraoka et al. |
| 2018/0220875 | A1 | 8/2018 | Hiratsuka |

FOREIGN PATENT DOCUMENTS

| EP | 1772095 | 4/2007 |
| EP | 2228002 | 9/2010 |
| JP | H06142081 | 5/1994 |
| JP | H06315458 | 11/1994 |
| JP | H06315459 | 11/1994 |
| JP | H07111967 | 5/1995 |
| JP | H07184831 | 7/1995 |
| JP | H07194516 | 8/1995 |
| JP | H0856900 | 3/1996 |
| JP | 2003305002 | 10/2003 |
| JP | 2005237659 | 9/2005 |
| JP | 2013000179 | 1/2013 |
| JP | 2017070519 | 4/2017 |
| WO | 2016199694 | 12/2016 |
| WO | 2017011535 | 1/2017 |

OTHER PUBLICATIONS

"International Search Report (Form PCT/ISA/210) of PCT/JP2018/022359," dated Aug. 21, 2018, with English translation thereof, pp. 1-5.

"Written Opinion of the International Searching Authority (Form PCT/ISA/237) of PCT/JP2018/022359," dated Aug. 21, 2018, with English translation thereof, pp. 1-11.

"Office Action of China Counterpart Application" with English translation thereof, dated Jul. 27, 2021, p. 1-p. 13.

"Search Report of Europe Counterpart Application", dated Jun. 24, 2020, p. 1-p. 7.

Office Action of Japan Counterpart Application, with English translation thereof, dated Feb. 22, 2021, pp. 1-10.

FIG. 19
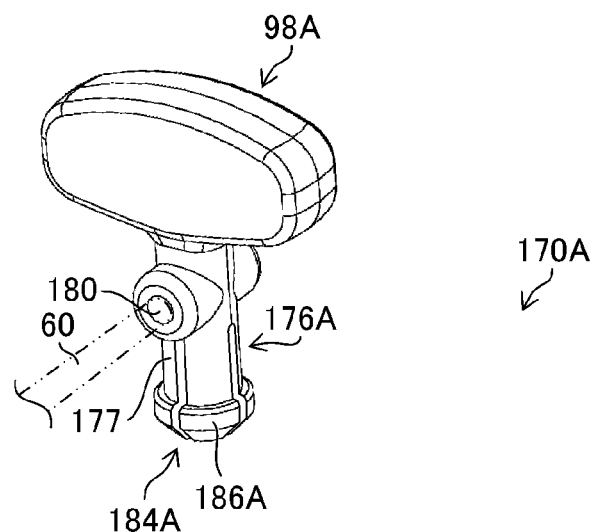
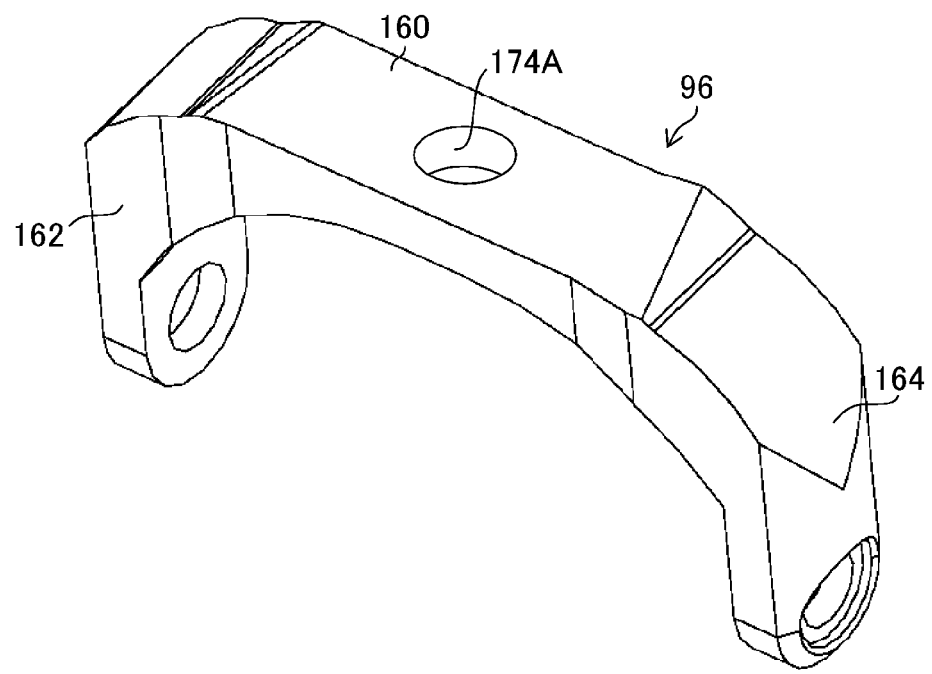

FIG. 23
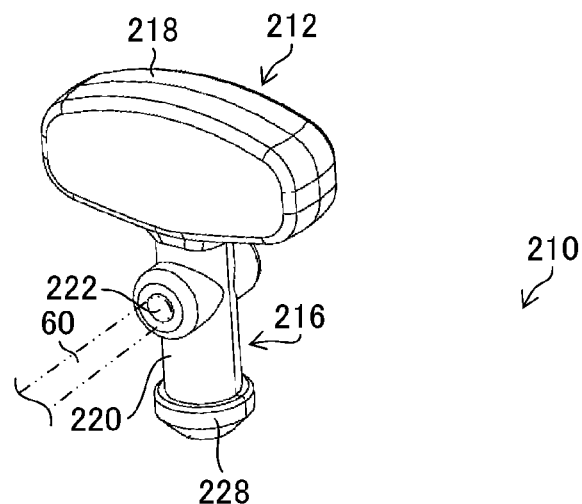
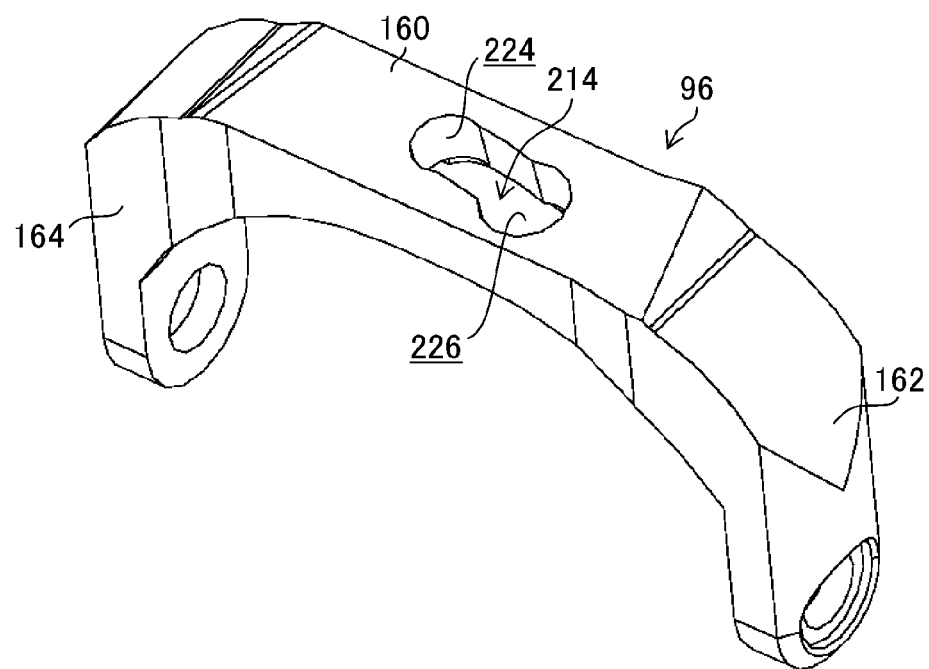

FIG. 26
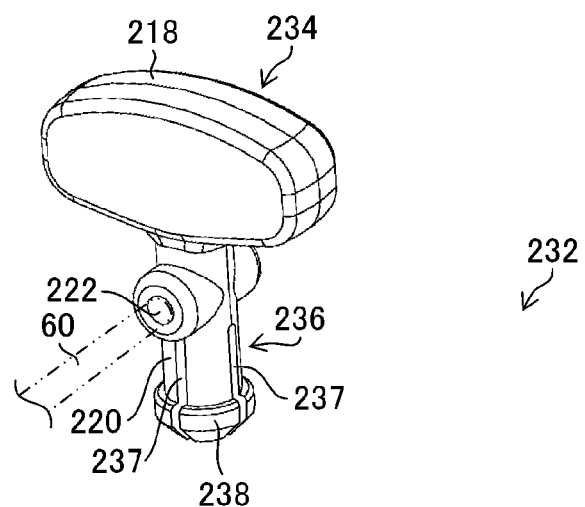
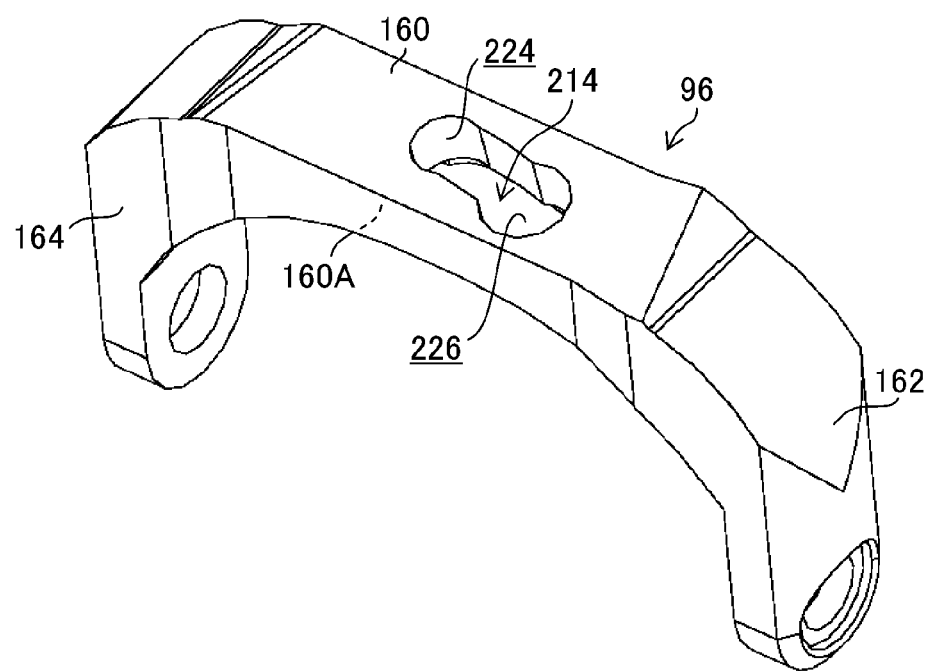

ENDOSCOPE

CROSS-REFERENCE TO RELATED APPLICATIONS

The present application is a Continuation of PCT International Application No. PCT/JP2018/022359 filed on Jun. 12, 2018 claiming priority under 35 U.S.C § 119(a) to Japanese Patent Application No. 2017-139137 filed on Jul. 18, 2017. Each of the above applications is hereby expressly incorporated by reference, in its entirety, into the present application.

BACKGROUND OF THE INVENTION

1. Field of the Invention

The present invention relates to endoscopes, and more particularly relates to an endoscope including a treatment tool erecting base that changes a lead-out direction of a treatment tool, at a distal end part of an insertion section.

2. Description of the Related Art

In an endoscope, one of various treatment tools is led in from a treatment tool lead-in port provided in a hand operation section (hereinafter, referred to as "operation section"), and the treatment tool is led out from a treatment tool lead-out port opening in a distal end member of an insertion section to the outside to be used for a treatment. For example, a treatment tool, such as forceps or a contrast agent tube, is used for a duodenum endoscope, and a treatment tool, such as a puncture needle, is used for an ultrasonic endoscope. With such a treatment tool, to provide a treatment at a desirable position in a subject, a lead-out direction of the treatment tool that is led out from the treatment tool lead-out port needs to be changed. Hence, the distal end member is provided with a treatment tool erecting base (hereinafter, referred to as "erecting base"), and the endoscope is provided with a treatment tool erecting mechanism that changes the posture of the erecting base between an erecting position and a lying position.

For the treatment tool erecting mechanism, a wire pulling mechanism is known (see JP1994-315458A (JP-H6-315458A)), in which a distal end portion of a wire (also referred to as forceps erecting wire) is directly attached to an erecting base. The mechanism couples the proximal end side of the wire to an erecting operation lever (also referred to as forceps erecting lever) included in an operation section, operates the wire to be pushed/pulled by using the erecting operation lever to rotate the erecting base around a rotation shaft, and hence changes the posture of the erecting base between an erecting position and a lying position.

More specifically, the operation section of JP1994-315458A (JP-H6-315458A) is provided with a grip part for holding the operation section with a hand, and an angle knob. The operation section has a wire opening portion below the grip part, and a drive shaft opening portion in the grip part. The proximal end of the wire is led out from the wire opening portion. The distal end of the drive shaft that is moved by the forceps erecting lever is led out from the drive shaft opening portion. The distal end of the drive shaft and the proximal end of the wire are removably coupled to a connecting tool. A protection cover that covers the connecting tool is provided on the operation section in an attachable/detachable manner.

When an endoscope is used for one of various inspections or one of various treatments, liquid in a body cavity adheres to the distal end member of the insertion section including the erecting base and to a guide pipe through which the wire is inserted. The endoscope after use is subjected to washing and disinfection processing using a washing solution and a disinfectant. At this time, since the guide pipe has a small diameter and the wire is inserted through the inside of the guide pipe, washing is troublesome.

Owing to this, in the endoscope of JP1994-315458A (JP-H6-315458A)), the cover covering the distal end member of the insertion section, the erecting base, and the wire are provided in an attachable/detachable manner; the cover, the erecting base, and the wire are removed; and the distal end member of the insertion section and the guide pipe of the wire are washed.

SUMMARY OF THE INVENTION

However, since the endoscope of JP1994-315458A (JP-H6-315458A) is configured such that the erecting operation mechanism that transmits the operating force of the forceps erecting lever to the wire is housed in the grip part of the operation section, the grip part increases in size.

In a typical endoscope, multiple contents, such as a base plate, an angle wire, a signal cable, an optical fiber bundle, an air/water supply tube, and a branch pipe, are densely arranged in a grip part (corresponding to a holding part) of the endoscope. Regarding such an endoscope, the endoscope of JP1994-315458A (JP-H6-315458A) requires the space for arranging the above-described erecting operation mechanism in the holding part. The holding part is increased in size as described above.

The present invention is made in light of the situations, and it is an object of the invention to provide an endoscope in which an erecting operation mechanism is provided at an operation section and that can prevent an increase in size of a holding part of the operation section.

To attain the object of the present invention, an endoscope according to the present invention includes an operation section having an operation section main body provided with an operating member, a holding part connected to the operation section main body, and an extension part extending from the holding part toward a distal end side; an insertion section that is provided on a distal end side of the extension part and that is inserted into a subject; a treatment tool erecting base provided at a distal end part of the insertion section; a movable member that is provided at the extension part and that moves in association with an operation of the operating member; an erecting operation wire that is coupled to the treatment tool erecting base at a distal end side thereof, that is coupled to the movable member at a proximal end side thereof, and that is pushed/pulled in accordance with a movement of the movable member to move the treatment tool erecting base; and an attachment member that is provided at a proximal end of the erecting operation wire and that is engaged with the movable member in an attachable/detachable manner by a one-touch operation.

According to an aspect of the present invention, preferably, the movable member is arranged to be exposed to outside of the extension part.

According to an aspect of the present invention, preferably, the endoscope includes a proximal end opening provided in the extension part; a distal end opening provided in the distal end part; and an erecting operation wire channel that is provided in the insertion section and that causes the proximal end opening to communicate with the distal end opening. The erecting operation wire is inserted through the erecting operation wire channel, has the distal end side that is arranged outside the distal end opening and that is coupled to the treatment tool erecting base, and has the proximal end side that is arranged outside the proximal end opening and that is coupled to the movable member.

According to an aspect of the present invention, preferably, an engagement hole is provided in one of the movable member and the attachment member, and an engagement portion that is engaged with the engagement hole in an attachable/detachable manner is provided at the other one.

According to an aspect of the present invention, preferably, the engagement portion is provided with an elastic deformation portion that is elastically deformed and engaged with the engagement hole.

According to an aspect of the present invention, preferably, a pair of claw portions are formed at the elastic deformation portion, the pair of claw portions being elastically deformable and configured to be latched to an edge portion of the engagement hole, the pair of claw portions being displaced in directions to move toward each other by elastic deformation when the engagement portion is engaged with or disengaged from the engagement hole.

According to an aspect of the present invention, preferably, the engagement hole has a small width portion having a first width, and a large width portion having a second width that is larger than the first width; and the engagement portion has a shaft portion having an outside diameter that is equal to or smaller than the first width, and a fall prevention portion that is provided at a distal end of the shaft portion, that has an outside diameter larger than the first width and smaller than the second width, and that restricts detachment of the shaft portion from the small width portion.

According to an aspect of the present invention, preferably, one of the movable member and the attachment member is provided with a cylindrical body extending in a direction perpendicular to an axial direction of the erecting operation wire, and the other one is provided with a ring-shaped body that is rotatably engaged with an outer periphery of the cylindrical body; and the endoscope includes a rotation restriction stopper that restricts relative rotations of the cylindrical body and the ring-shaped body.

According to an aspect of the present invention, preferably, the endoscope includes an engagement member provided at a distal end of the erecting operation wire; and a housing groove that is provided in the treatment tool erecting base and that is engaged with the engagement member in an engageable/disengageable manner.

According to an aspect of the present invention, preferably, the movable member is rotatably provided while a direction perpendicular to an axial direction of the erecting operation wire serves as a rotation axis.

According to an aspect of the present invention, preferably, the operating member is an operating member rotatably supported by the operation section; and the endoscope includes a first conversion mechanism that converts a rotational motion of the operating member into a linear motion, a drive member that is linearly driven by the first conversion mechanism, and a second conversion mechanism that converts a linear motion of the drive member into a rotational motion to rotate the movable member.

According to an aspect of the present invention, preferably, the second conversion mechanism includes a speed reduction mechanism.

With the present invention, in the endoscope in which the erecting operation mechanism is provided at the operation section, an increase in size of the holding part of the operation section can be prevented.

BRIEF DESCRIPTION OF THE DRAWINGS

FIG. 19 is an explanatory diagram illustrating a modification of the coupling structure according to the first embodiment;

FIG. 23 is an assembly perspective view of the coupling structure illustrated in FIG. 22;

FIG. 26 is an assembly perspective view of a coupling structure according to a third embodiment;

DESCRIPTION OF THE PREFERRED EMBODIMENTS

Endoscopes according to preferred embodiments of the present invention are described in detail below with reference to the accompanying drawings.

Figure 1:
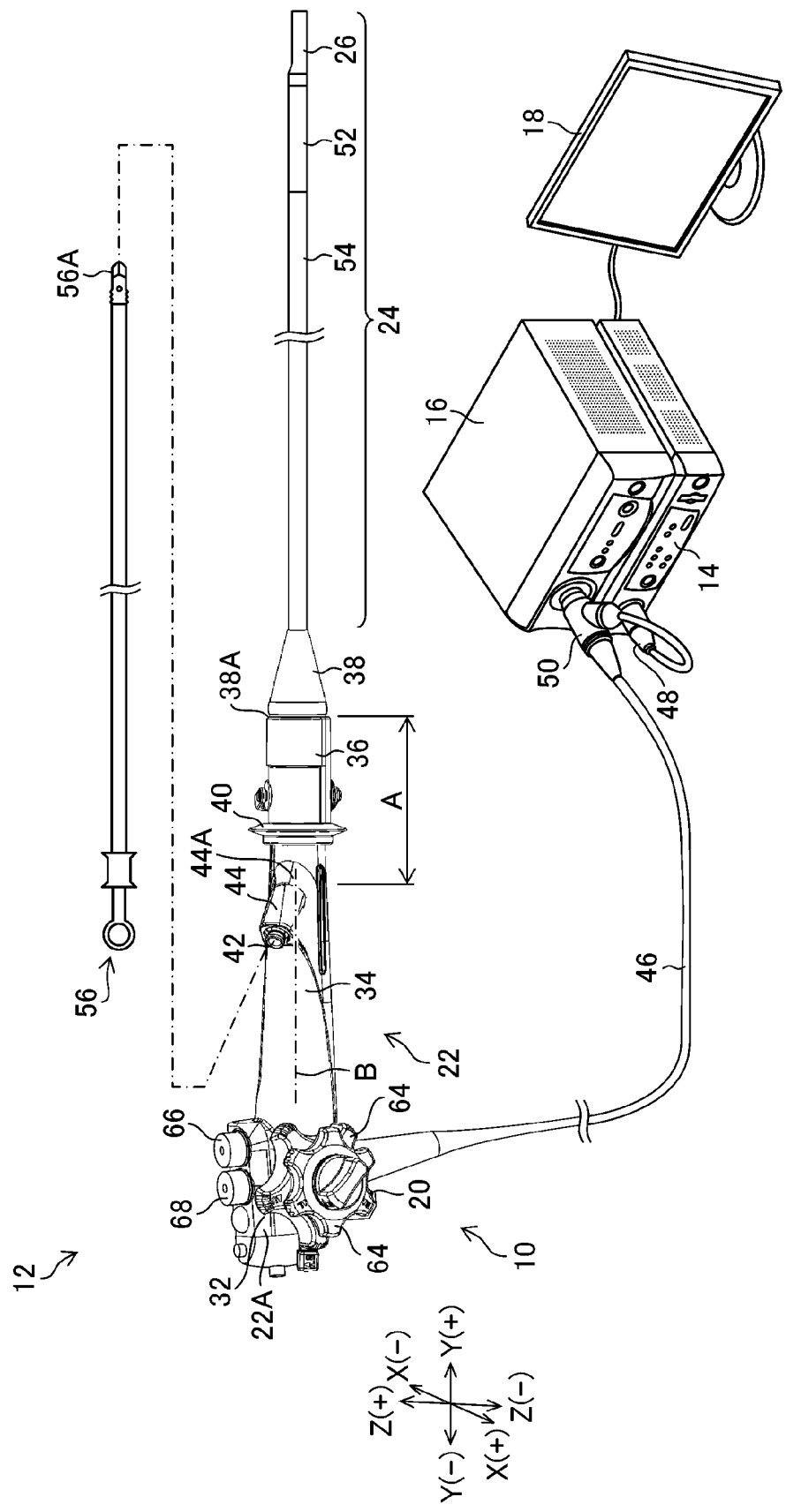
FIG. 1 is a configuration diagram of an endoscope system including an endoscope according to an embodiment.

FIG. 1 is a configuration diagram of an endoscope system 12 including an endoscope 10 according to an embodiment of the present invention. The endoscope system 12 includes an endoscope 10, a processor device 14, a light source device 16, and a display 18. FIG. 1 also illustrates a treatment tool 56 that is used in the endoscope system 12.

The endoscope 10 includes an operation section 22 including an erecting operation lever 20 that serves as an operating member, and an insertion section 24 provided on the distal end side of the operation section 22.

Figure 2:
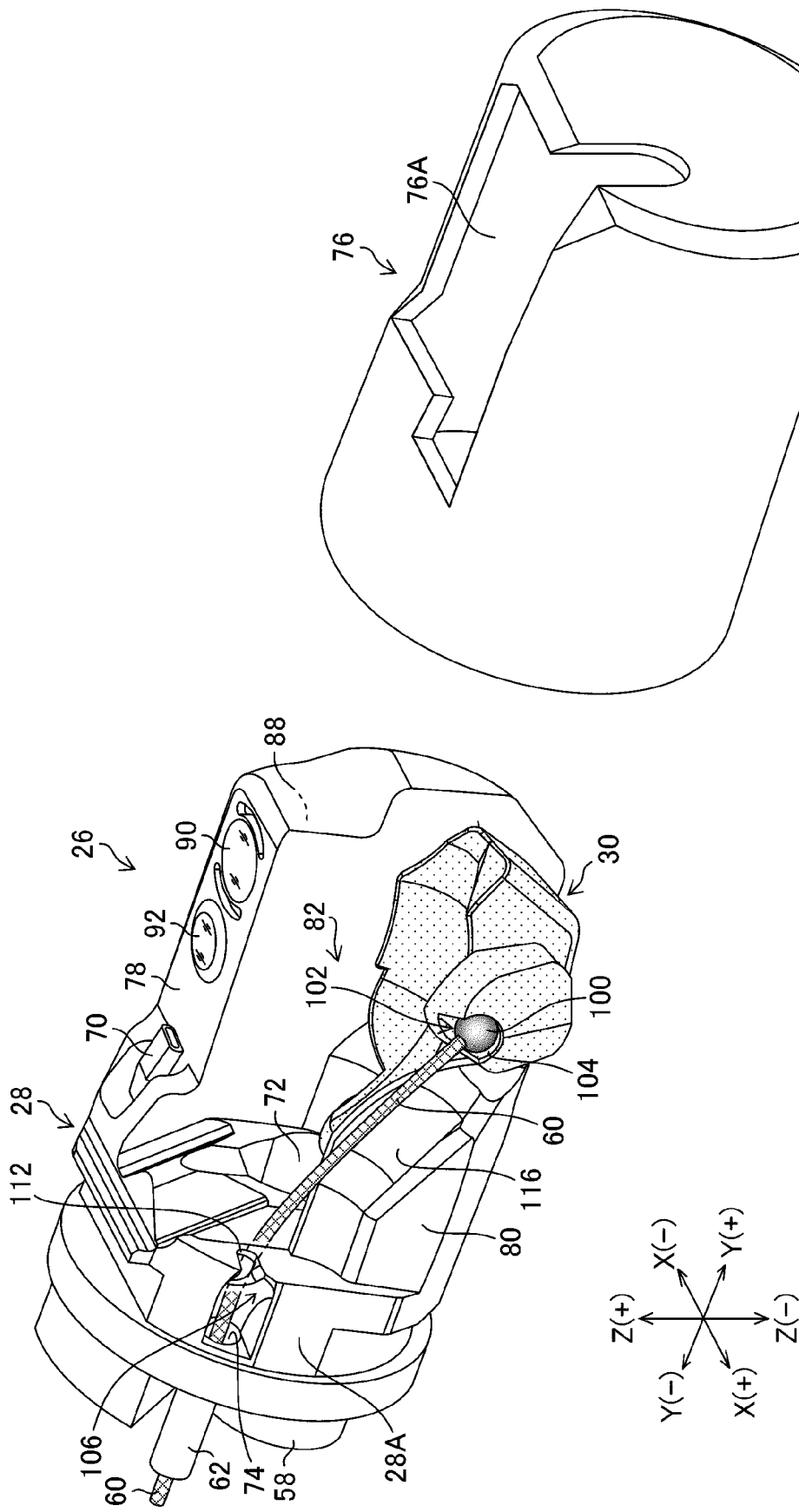
FIG. 2 is a perspective view of a distal end member when an erecting base is located at a lying position.
Figure 3:
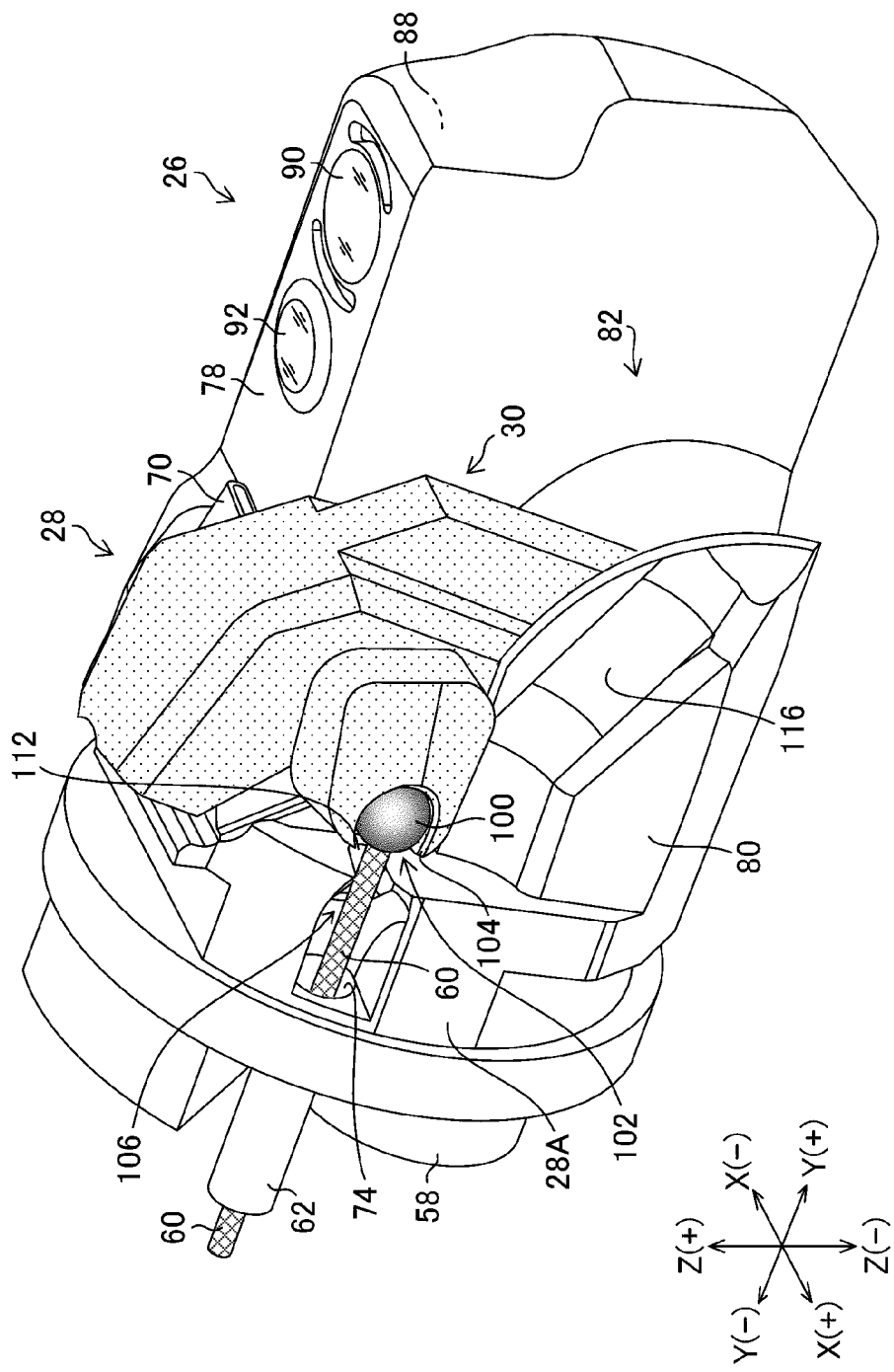
FIG. 3 is a perspective view of the distal end member when the erecting base is located at an erecting position.

Referring to perspective views in FIGS. 2 and 3 illustrating the configuration of a distal end part 26 of the insertion section 24, a distal end member 28 is provided at the distal end part 26 of the insertion section 24, and an erecting base 30 (described later) is attached to the distal end member 28. FIG. 2 is a perspective view of the distal end member 28 when the erecting base 30 is located at a lying position. FIG. 3 is a perspective view of the distal end member 28 when the erecting base 30 is located at an erecting position.

In the following description, an upward direction indicates a Z(+) direction in FIGS. 1 and 2, and a downward direction indicates a Z(−) direction in FIGS. 1 and 2. Moreover, a rightward direction indicates an X(+) direction in FIG. 2, and a leftward direction indicates an X(−) direction in FIG. 2. Furthermore, a Y(+) direction in FIGS. 1 and 2 indicates a distal end side direction of the distal end member 28, and a Y(−) direction in FIGS. 1 and 2 indicates a proximal end side direction of the distal end member 28.

Referring back to FIG. 1, the operation section 22 has an operation section main body 32 provided with the erecting operation lever 20, a holding part 34 connected to the operation section main body 32, and an extension part 36 extending from the holding part 34 toward the distal end side. A proximal end portion of the insertion section 24 is provided on the distal end side of the extension part 36 via a break prevention pipe 38. The holding part 34 is a part that is held by an operator during an operation of the endoscope 10.

The extension part 36 is a part in a non-holding region that is extended from a distal end portion of the holding part 34 toward the distal end side to provide part of components of a movable member 96 (described later, see FIG. 6) and an erecting operation mechanism 120 (described later, see FIGS. 9 and 10) on the extension part 36. Specifically, a region A extending from a distal end portion 44A of a protruding mount portion 44 of a treatment tool lead-in port 42 provided in the holding part 34 to a proximal end portion 38A of the break prevention pipe 38 corresponds to the extension part 36. A circular-ring-shaped flange 40 is provided in the region of the extension part 36.

The operation section main body 32 of the operation section 22 includes a universal cord 46. A light source connector 50 is provided on the distal end side of the universal cord 46. An electric connector 48 branches out from the light source connector 50. The electric connector 48 is connected to the processor device 14, and the light source connector 50 is connected to the light source device 16.

The insertion section 24 includes the distal end part 26, a bending part 52, and a soft part 54 that are coupled from the distal end side toward the proximal end side.

The insertion section 24 incorporates the following contents. In particular, the contents include, for example, a treatment tool channel 58 that guides a distal end portion 56A of the treatment tool 56 in FIG. 1 to the distal end member 28 in FIG. 2; an erecting operation wire 60 (hereinafter, referred to as wire 60) for performing an operation of changing a lead-out direction of the distal end portion 56A of the treatment tool 56 led out from the distal end member 28; an erecting operation wire channel 62 (hereinafter, referred to as wire channel 62) that guides a distal end portion of the wire 60 to the distal end member 28; a light guide (not illustrated) that guides illumination light supplied from the light source device 16 in FIG. 1 to the distal end member 28 in FIG. 2; an air/water supply tube (not illustrated); an angle wire (not illustrated); and a signal cable (not illustrated).

Referring back to FIG. 1, the operation section 22 is formed in a substantially cylindrical shape as a whole and has a cylinder axis B along the Y(+)-Y(−) direction. A pair of angle knobs 64 that perform an operation of bending the bending part 52 are arranged at a side surface 22A on one side with respect to a section extending in the up-down direction and including the cylinder axis B of the operation section 22. The pair of angle knobs 64 are coaxially rotatably provided.

The bending part 52 has a structure in which a plurality of angle rings (not illustrated) are mutually rotatably coupled. The bending part 52 is configured such that the outer periphery of the structure is covered with a tubular mesh body braided using metal wires, and the outer peripheral surface of the mesh body is covered with a tubular outer sheath made of rubber. For example, four angle wires (not illustrated) are disposed to extend from the thus configured bending part 52 to the angle knobs 64. An operation of pushing/pulling the angle wires is performed by an operation of rotating the angle knobs 64 to bend the bending part 52 upward, downward, leftward, and rightward.

Moreover, on the operation section main body 32 of the operation section 22, an air/water supply button 66 and a suction button 68 are arranged side by side. By operating the air/water supply button 66, the air and water can be ejected from an air/water supply nozzle 70 provided in the distal end member 28 in FIG. 2. By operating the suction button 68 in FIG. 1, body fluids such as blood can be sucked from a suction port that also serves as a treatment tool lead-out port 72 provided in the distal end member 28 in FIG. 2.

Furthermore, the treatment tool lead-in port 42 is provided in the holding part 34 of the operation section 22 in FIG. 1. The treatment tool 56 is led in to the treatment tool lead-in port 42. The treatment tool 56 led in from the treatment tool lead-in port 42 while the distal end portion 56A is at the head is inserted through the treatment tool channel 58 in FIG. 2 inserted through the insertion section 24, and is led out to the outside from the treatment tool lead-out port 72 provided in the distal end member 28.

The erecting operation lever 20 is rotatably provided at the one side surface 22A of the operation section 22 in FIG. 1 in a manner coaxial with the angle knobs 64. The erecting operation lever 20 is rotationally operated by a hand of the operator who holds the holding part 34. When the erecting operation lever 20 is rotationally operated, the wire 60 in FIG. 2 is pushed/pulled by the erecting operation mechanism 120 (see FIGS. 9 and 10) that moves in association with the rotational operation of the erecting operation lever 20, and the posture of the erecting base 30 coupled to the distal end side of the wire 60 is changed between an erecting position in FIG. 3 and a lying position in FIG. 2. The above-described erecting operation mechanism 120 will be described later.

The soft part 54 illustrated in FIG. 1 has a helical pipe (not illustrated) formed by winding a thin elastic strip-shaped plate made of metal in a helical form. The outside of the helical pipe of the soft part 54 is covered with a tubular mesh body braided using metal wires. The outer peripheral surface of the mesh body is covered with a tubular outer sheath made of resin.

The endoscope 10 according to the thus configured embodiment is a side-view endoscope used as a duodenum endoscope. The insertion section 24 is inserted into a subject via the oral cavity. The insertion section 24 is inserted from the esophagus via the stomach to the duodenum, and, for example, a treatment, such as a predetermined inspection or a predetermined medical care, is performed.

In the embodiment, biopsy forceps serve as an example of the treatment tool 56, the biopsy forceps having a cup capable of collecting a living tissue at the distal end portion 56A. However, it is not limited thereto. For example, a treatment tool, such as a contrast agent tube or an endoscopic sphincterotomy (EST) knife, is used as another treatment tool.

Next, the distal end part 26 of the insertion section 24 is described.

Referring to FIG. 2, the distal end part 26 of the insertion section 24 is configured of the distal end member 28, and a cap 76 that is mounted on the distal end member 28 in an attachable/detachable manner. The cap 76 has a substantially tubular shape whose distal end side is sealed. A substantially rectangular opening window 76A is formed in part of the outer peripheral surface of the cap 76. When the cap 76 is mounted on the distal end member 28, the opening window 76A of the cap 76 communicates with the treatment tool lead-out port 72 of the distal end member 28. Thus, the distal end portion 56A of the treatment tool 56 led out from the treatment tool lead-out port 72 is led out to the outside from the opening window 76A.

The cap 76 is made of an elastic material, for example, a rubber material, such as fluorocarbon rubber or silicon rubber; or a resin material such as polysulfone. An engagement portion (not illustrated) is provided on the proximal end side of the cap 76. The engagement portion is engaged with a groove (not illustrated) formed in the distal end member 28. By engaging the engagement portion with the groove of the distal end member 28, the cap 76 is mounted on the distal end member 28. When the treatment with the endoscope 10 is ended, the cap 76 is removed from the distal end member 28, and washed and disinfected, or discarded as a disposable.

The distal end member 28 is made of a corrosion-resistant metal material. Moreover, in the distal end member 28, a partition wall 78 protruding toward the distal end side and a partition wall 80 opposite to the partition wall 78 are integrally provided. An erecting base housing chamber 82 that houses the erecting base 30 is formed between the partition wall 78 and the partition wall 80. The treatment tool lead-out port 72 that leads out the treatment tool 56 to the outside is formed on the proximal end side of the erecting base housing chamber 82. A distal end portion of the treatment tool channel 58 is connected to the treatment tool lead-out port 72.

The treatment tool channel 58 is inserted through the inside of the insertion section 24 in FIG. 1. A proximal end portion of the treatment tool channel 58 is connected to a distal end pipe 202 of a branch pipe 200 (see FIG. 10) provided in the operation section 22.

The branch pipe 200 has a known structure. A proximal end portion of the branch pipe 200 is branched into two pipe lines 204 and 206. The treatment tool lead-in port 42 is formed at the proximal end of the one pipe line 204. The distal end portion 56A of the treatment tool 56 led in from the treatment tool lead-in port 42 to the treatment tool channel 58 via the pipe line 204 is inserted through the treatment tool channel 58, and is led out from the treatment tool lead-out port 72 in FIG. 2 to the erecting base housing chamber 82. The lead-out direction of the distal end portion 56A of the treatment tool 56 led out to the erecting base housing chamber 82 is changed in accordance with the posture between the erecting position and the lying position of the erecting base 30 arranged in the erecting base housing chamber 82. Moreover, the distal end of a suction pipe 208 for sucking body fluids such as blood is connected to the proximal end of the other pipe line 206 of the branch pipe 200 illustrated in FIG. 10.

Figure 4:
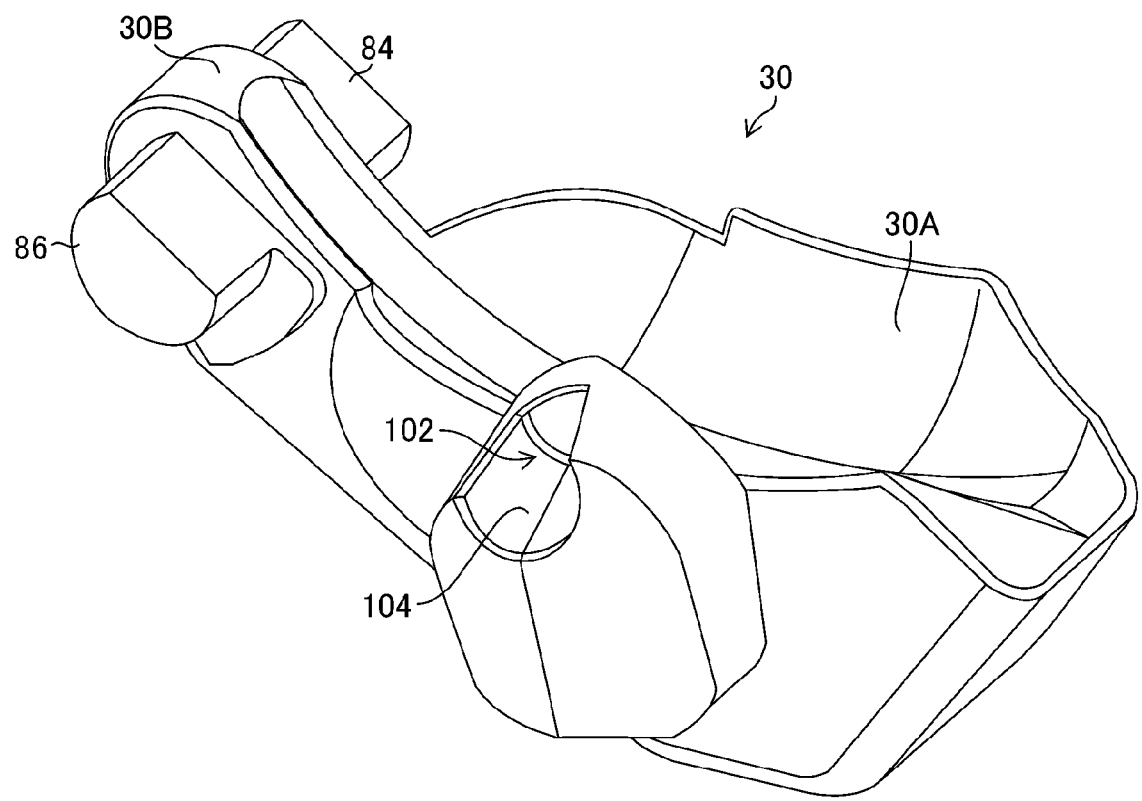
FIG. 4 is an enlarged perspective view of the erecting base.

FIG. 4 is an enlarged perspective view of the erecting base 30. Referring to FIG. 4, a guide surface 30A is included in an upper surface of the erecting base 30. Along the guide surface 30A, the distal end portion 56A of the treatment tool 56 in FIG. 1 is led out to the outside from the opening window 76A of the cap 76 in FIG. 2.

Referring to FIG. 4, the erecting base 30 includes rotation shafts 84 and 86 on both side surfaces of a base portion 30B of the erecting base 30. The axial direction of the rotation shafts 84 and 86 is set in the X(+)-X(−) direction in FIG. 2 when the erecting base 30 is attached to the distal end member 28.

Figure 5:
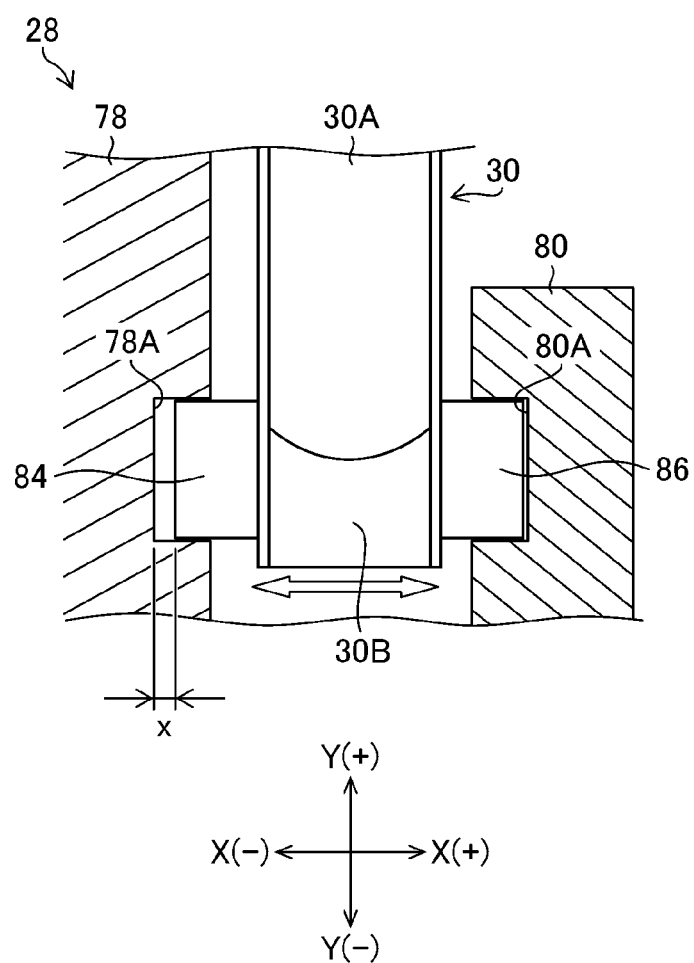
FIG. 5 is a main-part sectional view illustrating an attachment structure of the erecting base to the distal end member.

FIG. 5 is a main-part sectional view illustrating an attachment structure of the erecting base 30 to the distal end member 28. Referring to FIG. 5, the axes of the rotation shafts 84 and 86 are coaxially arranged via the base portion 30B of the erecting base 30. The rotation shaft 84 is rotatably fitted to a recessed bearing portion 78A of the partition wall 78. The rotation shaft 86 is rotatably fitted to a recessed bearing portion 80A of the partition wall 80. Moreover, the rotation shafts 84 and 86 are mounted at the bearing portions 78A and 80A respectively with a predetermined backlash amount x in the axial direction of the rotation shafts 84 and 86. When the rotation shafts 84 and 86 are moved to one side by using the backlash amount x, a portion of one bearing portion of the bearing portions 78A and 80A is exposed, and a brush can be easily inserted to the exposed portion, thereby increasing washing efficiency of the bearing portions 78A and 80A.

Referring to FIGS. 2 and 3, an optical system housing chamber 88 is included in the partition wall 78. An illumination window 90 and an observation window 92 are adjacently disposed at an upper portion of the optical system housing chamber 88. In addition, the air/water supply nozzle 70 directed to the observation window 92 is provided at the distal end member 28. The air/water supply nozzle 70 is connected to an air/water supply device (not illustrated) via an air/water supply tube (not illustrated) inserted through the insertion section 24. By operating the air/water supply button 66 of the operation section 22 illustrated in FIG. 1, the air or water is ejected from the air/water supply nozzle 70 toward the observation window 92. Accordingly, the observation window 92 is washed.

An illumination unit (not illustrated) and an imaging unit (not illustrated) are housed in the optical system housing chamber 88. The illumination unit includes an illumination lens (not illustrated) disposed inside the illumination window 90 and a light guide (not illustrated) arranged such that a distal end surface of the light guide faces the illumination lens. The light guide is disposed to extend from the insertion section 24 via the operation section 22 to the universal cord 46 of the endoscope 10, and the proximal end thereof is connected to the light source device 16 via the light source connector 50. Thus, the irradiation light from the light source device 16 is transmitted through the light guide and is emitted from the illumination window 90 to the outside.

The above-described imaging unit includes an imaging optical system (not illustrated) disposed inside the observation window 92 and an imaging element (not illustrated) of a complementary metal oxide semiconductor (CMOS) or a charge coupled device (CCD). The imaging element is connected to the processor device 14 via a signal cable (not illustrated) inserted through the insertion section 24 in FIG. 1. An imaging signal of a subject image obtained by the imaging unit is output to the processor device 14 via the signal cable, undergoes image processing, and then is displayed as a subject image on the display 18.

Figure 6:
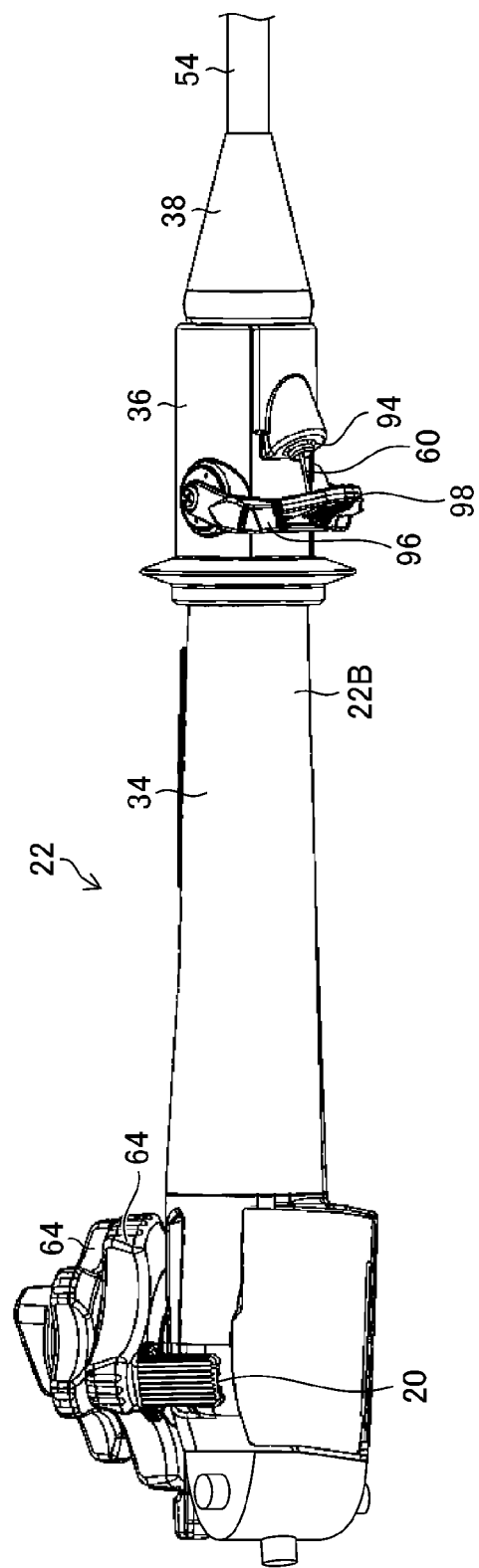
FIG. 6 is a perspective view illustrating the other side surface opposite to one side surface of an operation section illustrated in FIG. 1.

Although the description is redundant, the wire 60 is described. Referring to FIGS. 2 and 3, the distal end side of the wire 60 is arranged outside a lead-out port 74 and is coupled to the erecting base 30. The proximal end side of the wire 60 is arranged outside a lead-in port 94 provided in the operation section 22 as illustrated in FIG. 6, and is coupled to the movable member 96 (see FIG. 10). The lead-out port 74 is an example of a distal end opening according to the present invention. The lead-in port 94 is an example of a proximal end opening according to the present invention.

FIG. 6 is a perspective view of the operation section 22, and is a perspective view illustrating the other side surface 22B opposite to the one side surface 22A of the operation section 22 illustrated in FIG. 1.

Referring to FIG. 6, the lead-in port 94 is provided in the extension part 36 of the operation section 22. An attachment member 98 is provided at the proximal end of the wire 60 arranged at the outside from the lead-in port 94. The attachment member 98 is mounted at an engagement hole (described later) of the movable member 96 in an attachable/detachable manner.

The extension part 36 of the operation section 22 is provided with the movable member 96. The movable member 96 is arranged to be exposed to the outside of the extension part 36. The movable member 96 moves in association with the operation of the erecting operation lever 20 by the erecting operation mechanism 120 (described later). In the embodiment, the movable member 96 is rotatably arranged at the other side surface 22B opposite to the one side surface 22A provided with the angle knobs 64. However, the arrangement position of the movable member 96 with respect to the extension part 36 is not limited, and may be rotatably arranged at a predetermined position of the extension part 36. The movable member 96 is a driven lever that rotates in association with the rotational operation of the erecting operation lever 20.

The erecting operation mechanism 120 is arranged inside the operation section 22. The erecting operation mechanism 120 moves the movable member 96 in association with the operation of the erecting operation lever 20. Thus, when the erecting operation lever 20 is operated, the movable member 96 moves via the erecting operation mechanism 120, and the wire 60 (see FIG. 2) coupled to the movable member 96 is pushed/pulled. The erecting operation mechanism 120 will be described later.

Next, an engagement structure for engaging the distal end of the wire 60 with the erecting base 30 in an engageable/disengageable manner is described.

Referring back to FIGS. 2 and 3, the distal end of the wire 60 is provided with an engagement member 100. Moreover, the erecting base 30 is provided with a housing groove 102 having an opening 104 formed on the side in the X(+) direction. The engagement member 100 is engaged with the housing groove 102 in an engageable/disengageable manner. Accordingly, by housing the engagement member 100 provided at the distal end of the wire 60 in the housing groove 102 via the opening 104, the distal end of the wire 60 is coupled to the erecting base 30.

In the embodiment, the engagement member 100 is a sphere, and the housing groove 102 is a spherical-surface-shaped concave portion that houses the spherical engagement member 100. The shapes of the engagement member 100 and the housing groove 102 are not limited to the above-described shapes. However, as long as the engagement member 100 is the sphere and the housing groove 102 is the spherical-surface-shaped concave portion, the sliding resistance between the engagement member 100 and the housing groove 102 generated by the pushing/pulling operation of the wire 60 can be decreased. Accordingly, the pushing/pulling operation of the wire 60 can be smoothly performed.

Moreover, the distal end member 28 includes an engagement guide portion 106 connected to the housing groove 102 at the erecting position in FIG. 3. The engagement guide portion 106 includes a function of guiding the engagement member 100 led out from the lead-out port 74 to the opening 104 of the housing groove 102. The lead-out port 74 is provided in the distal end member 28, and communicates with the lead-in port 94 (see FIG. 6) via the wire channel 62 provided in the insertion section 24.

With the endoscope 10 having such an engagement guide portion 106, when the wire 60 is led in from the lead-in port 94 while the engagement member 100 is at the head, the engagement member 100 is inserted through the wire channel 62 (see FIG. 2) and is led out to the outside from the lead-out port 74. The engagement member 100 is guided by the engagement guide portion 106 toward the opening 104 of the housing groove 102 of the erecting base 30 through the ongoing lead-in operation of the wire 60, and is engaged with the housing groove 102 from the opening 104. Accordingly, with the endoscope 10 according to the embodiment, the engagement member 100 of the wire 60 can be engaged with the housing groove 102 of the erecting base 30 only by the lead-in operation of the wire 60.

Figure 7:
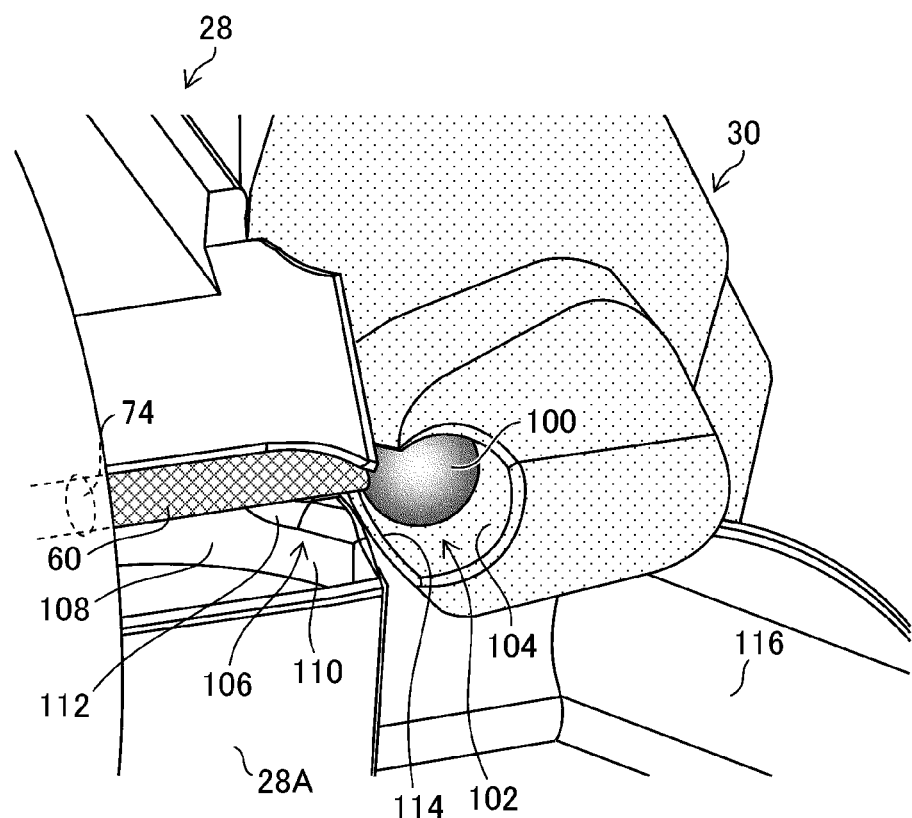
FIG. 7 is an enlarged perspective view when an engagement portion is housed in a housing portion via an engagement guide portion.
Figure 8:
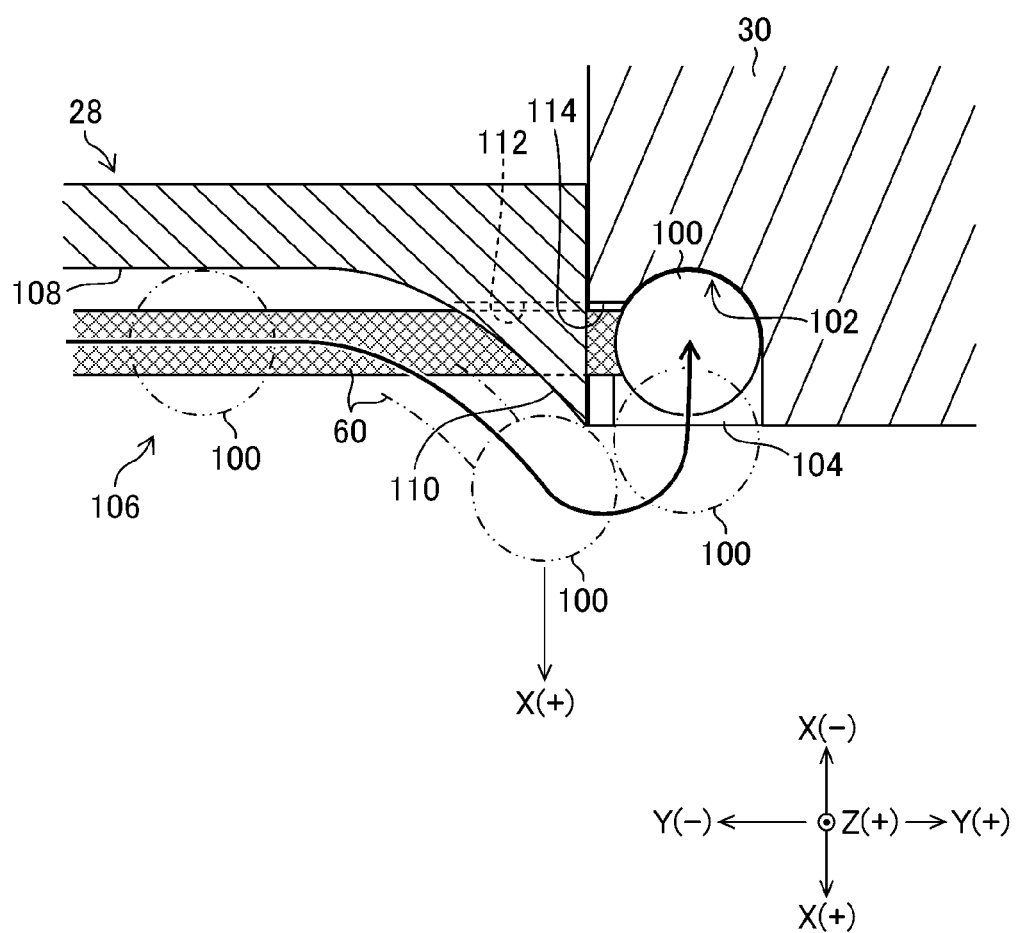
FIG. 8 is a movement explanatory diagram when the engagement portion is guided by the engagement guide portion and housed in the housing portion.

FIG. 7 is an enlarged perspective view when the engagement member 100 is engaged with the housing groove 102 via the engagement guide portion 106. FIG. 8 is an explanatory diagram illustrating a successive movement until the engagement member 100 is guided by the engagement guide portion 106 and engaged with the housing groove 102.

Referring to FIGS. 7 and 8, the engagement guide portion 106 includes an engagement guide path 108 that guides the engagement member 100 led out from the lead-out port 74 to the opening 104 of the housing groove 102, and a deformation generation portion 110 connected to the opening 104 of the housing groove 102 in the engagement guide path 108. The deformation generation portion 110 comes into contact with the engagement member 100 that advances in the Y(+) direction toward the opening 104 in the engagement guide path 108, and guides the engagement member 100 in the X(+) direction while guiding the engagement member 100 in the Y(+) direction.

Accordingly, the distal end side of the wire 60 is elastically deformed in a direction (X(+) direction) to move gradually away from the opening 104 as the engagement member 100 approaches the opening 104 along the engagement guide path 108. When the engagement member 100 has passed through the deformation generation portion 110, the engagement member 100 advancing in the engagement guide path 108 moves in the X(−) direction by the resilient force of the wire 60, and is engaged with the housing groove 102 from the opening 104.

The engagement guide path 108 is formed by cutting a portion of a peripheral surface 28A of the distal end member 28 into a recessed shape, and is a surface that extends from the lead-out port 74 in the Y(+) direction and that is gradually inclined in the X(+) direction. The deformation generation portion 110 is formed on the distal end side of the engagement guide path 108.

Moreover, a groove 112 is formed in the engagement guide portion 106. When the engagement member 100 is engaged with the housing groove 102, the groove 112 allows the distal end side of the wire 60 to fall thereinto and to retract therein. Furthermore, a groove 114 is also formed at the proximal end side of the housing groove 102 of the erecting base 30. When the engagement member 100 is engaged with the housing groove 102, the groove 114 allows the distal end side of the wire 60 to fall thereinto and to retract therein. The width dimension of the groove 112 in a direction orthogonal to the paper face of FIG. 8 is larger than the diameter of the wire 60, and is smaller than the diameter of the engagement member 100 so that the engagement member 100 which passes through the deformation generation portion 110 does not fall into the groove 112. The width dimension of the groove 114 in the direction orthogonal to the paper face of FIG. 8 is larger than the diameter of the wire 60, and is smaller than the diameter of the engagement member 100 so that the engagement member 100 engaged with the housing groove 102 does not come out in the Y(−) direction.

The engagement guide portion 106 has a suitable form for a case where the engagement member 100 is engaged with the housing groove 102 in a state in which the erecting base 30 is located at the erecting position. That is, referring to FIG. 7, the housing groove 102 is arranged at a position facing the lead-out port 74 in the state in which the erecting base 30 is located at the erecting position. Thus, by advancing the engagement member 100 straight from the lead-out port 74, the engagement member 100 can be engaged with the housing groove 102 of the erecting base 30 located at the erecting position, via the engagement guide portion 106.

Next, a detachment structure for detaching the engagement member 100 of the wire 60 engaged with the housing groove 102 of the erecting base 30 from the housing groove 102 is described.

The distal end member 28 includes a detachment guide surface 116. The detachment guide surface 116 is included in an upper surface of the partition wall 80 (see FIG. 2). The detachment guide surface 116 is a guide surface that extends in the X(+) direction and that is inclined in the Z(−) direction (see FIGS. 2 and 3). The detachment guide surface 116 also functions as a surface that guides the wire 60 in a direction in which the engagement member 100 is detached from the inside of the housing groove 102 to the outside of the opening 104 when the wire 60 is operated to be further pushed in a state in which the engagement member 100 is engaged with the housing groove 102 and the erecting base 30 is located at the lying position.

With the thus configured detachment structure, an attachment member (described later) provided at the proximal end of the wire 60 is detached from an engagement hole (described later) of the movable member 96, and then the wire 60 is operated to be pushed from the lead-in port 94 of the extension part 36 to cause the erecting base 30 to be located at the lying position in FIG. 2 from the erecting position in FIG. 3. Then, by further operating the wire 60 to be pushed, the wire 60 is guided in the X(+) direction in which the engagement member 100 is detached from the inside of the housing groove 102 to the outside of the opening 104 by using the detachment guide surface 116 of the distal end member 28. Accordingly, the engagement member 100 is easily detached to the outside of the opening 104 from the inside of the housing groove 102 by the resilient force of the wire 60.

Next, the erecting operation mechanism 120 is described.

Figure 9:
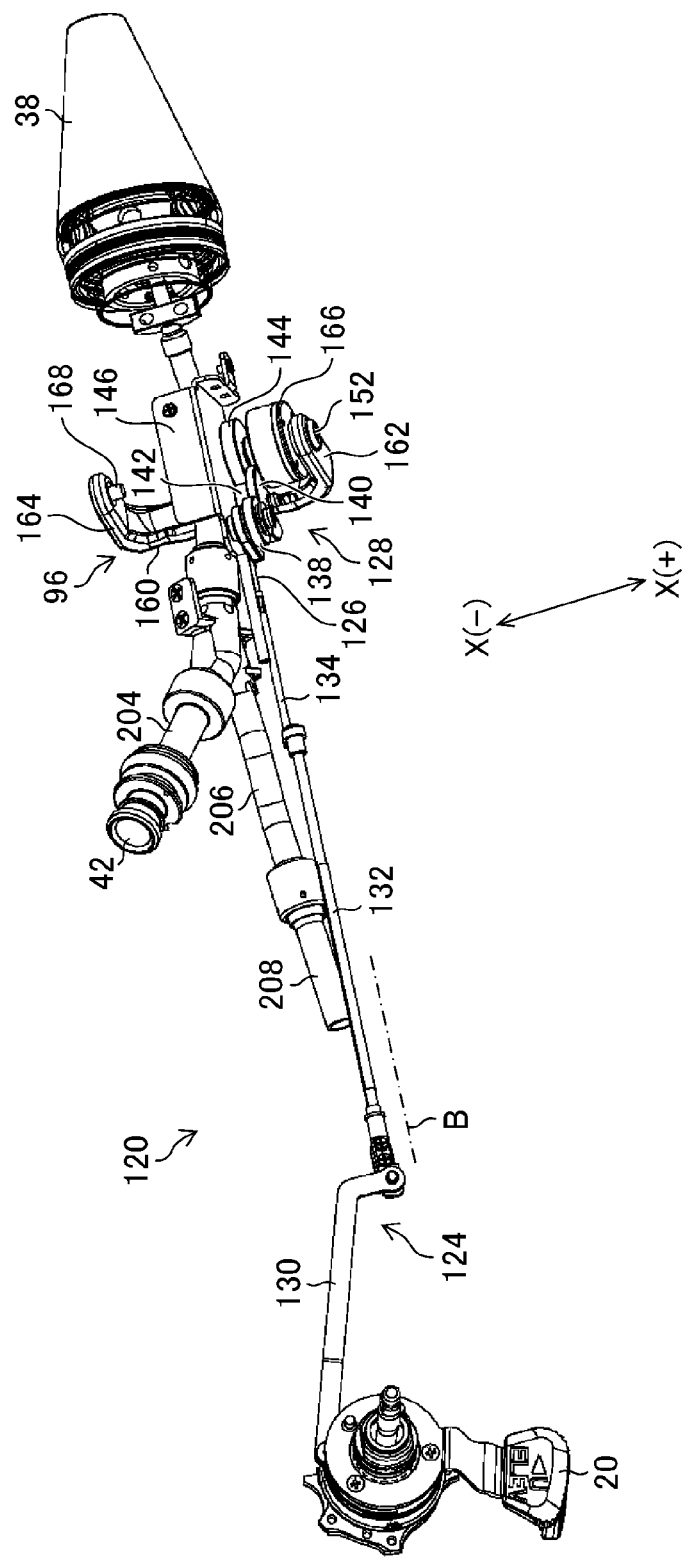
FIG. 9 is a configuration diagram illustrating the entire configuration of an erecting operation mechanism.
Figure 10:
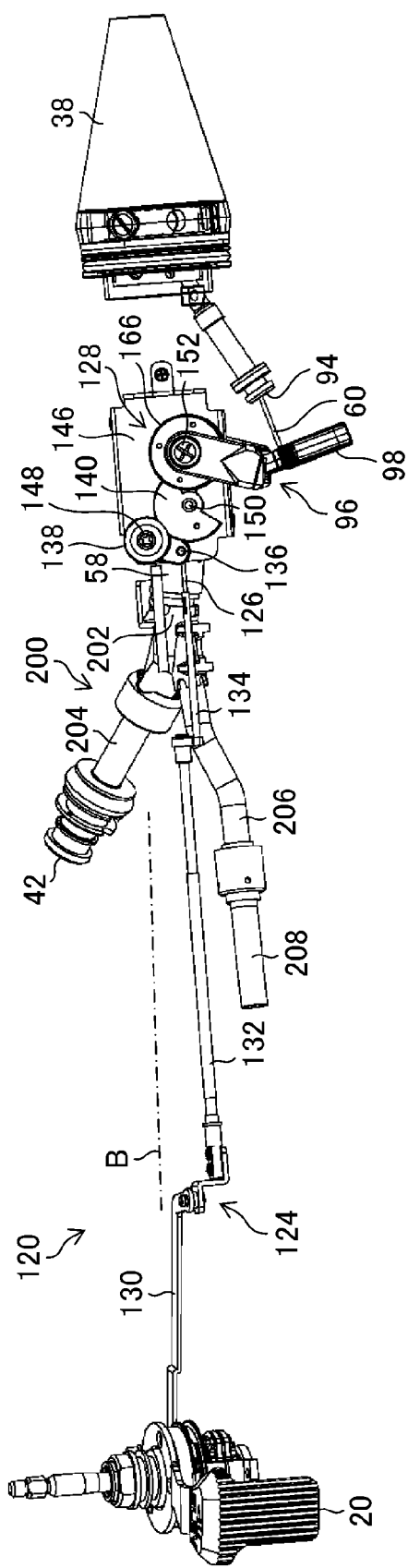
FIG. 10 is a side view of the erecting operation mechanism in FIG. 9.

FIG. 9 is a configuration diagram illustrating the entire configuration of the erecting operation mechanism 120. FIG. 10 is a side view of the erecting operation mechanism 120 in FIG. 9. FIGS. 9 and 10 omit illustration of an exterior case (not illustrated) of the operation section 22, and illustrate the inside of the operation section 22.

As illustrated in FIGS. 9 and 10, the erecting operation mechanism 120 is provided in the operation section 22. Specifically, in the operation section 22, components of respective portions configuring the erecting operation mechanism 120 are provided in an area from the operation section main body 32 to the extension part 36.

The erecting operation mechanism 120 is also a power transmission mechanism that couples the erecting operation lever 20 and the movable member 96 to each other and that transmits a rotational movement of the erecting operation lever 20 to the movable member 96.

The erecting operation mechanism 120 includes a first conversion mechanism 124 that converts a rotational motion of the erecting operation lever 20 into a linear motion, a wire 126 that is linearly moved by the first conversion mechanism 124, and a second conversion mechanism 128 that converts the linear motion of the wire 126 into a rotational motion to rotate the movable member 96. The wire 126 is an example of a drive member according to the present invention.

The first conversion mechanism 124 includes a crank member 130 whose proximal end is coupled to the erecting operation lever 20, a first slider 132 whose proximal end is coupled to the distal end of the crank member 130, and a second slider 134 whose proximal end is coupled to the distal end of the first slider 132.

The proximal end of the wire 126 is connected to the distal end of the second slider 134. The distal end of the wire 126 is connected to the second conversion mechanism 128 including a speed reduction mechanism.

With the thus configured first conversion mechanism 124, when the erecting operation lever 20 is rotationally operated, the crank member 130, the first slider 132, and the second slider 134 linearly move along the cylinder axis B in association with the rotational operation. Accordingly, the wire 126 linearly moves along the cylinder axis B, and the linear motion is transmitted to the second conversion mechanism 128.

The second conversion mechanism 128 includes a lever 136, a first gear 138, a second gear 140, a third gear 142, and a fourth gear 144. The first gear 138, the second gear 140, the third gear 142, and the fourth gear 144 configure the speed reduction mechanism.

The lever 136 is rotatably supported by a bracket 146 via a shaft 148. The distal end of the wire 126 is coupled to the lever 136. Thus, the lever 136 is rotated around the shaft 148 by the linear motion of the wire 126.

The first gear 138 is provided integrally with the lever 136, and is rotated around the shaft 148. The second gear 140 is meshed with the first gear 138, and is rotatably supported by the bracket 146 via a shaft 150. The third gear 142 is provided integrally with the second gear 140, and is provided coaxially with the second gear 140. The fourth gear 144 is provided coaxially with a drive shaft 152 of the movable member 96, and is rotatably supported together with the movable member 96 by the bracket 146 via the drive shaft 152. The fourth gear 144 is meshed with the third gear 142.

With the thus configured second conversion mechanism 128, when the linear motion of the wire 126 is transmitted to the lever 136, the first gear 138 is rotationally operated together with the lever 136, the rotational movement of the first gear 138 is transmitted to the fourth gear 144 via the second gear 140 and the third gear 142, and hence the fourth gear 144 is rotated. Accordingly, the movable member 96 integrated with the fourth gear 144 is rotated around the drive shaft 152.

Thus, with the thus configured erecting operation mechanism 120, the rotational operation of the erecting operation lever 20 can be transmitted to the movable member 96 via the first conversion mechanism 124, the wire 126, and the second conversion mechanism 128. Accordingly, the movable member 96 is rotated around the drive shaft 152.

With the erecting operation mechanism 120, the speed of the rotational movement of the erecting operation lever 20 is reduced by the second conversion mechanism 128 including the speed reduction mechanism, and then the rotational movement is transmitted to the movable member 96. That is, the rotation angle of leg portions 162 and 164 of the movable member 96 becomes smaller than the rotation angle of the lever 136 that moves by the operation of the erecting operation lever 20. Accordingly, the force required for operating the erecting operation lever 20 can be further decreased, and the erecting/lying posture of the erecting base 30 can be easily controlled by the erecting operation lever 20. The second conversion mechanism 128 is arranged in the extension part 36, and configures part of components of the erecting operation mechanism 120 together with the movable member 96.

In the embodiment, the wire 126 is an example of a drive member of the erecting operation mechanism 120 as illustrated in FIGS. 9 and 10. Since the wire 126 is used as the drive member, the following advantages are attained. That is, when the linear motion of the second slider 134 is converted into the rotational motion of the lever 136, the wire 126 has a motion in a curve form (loose), hence a link mechanism is not required to be disposed, and limitation on the space is reduced. When the second slider 134 and the lever 136 are coupled to each other by a link mechanism, a place to which the force escapes is decreased in the erecting operation mechanism 120. In such a case, by using the wire 126, the wire 126 is loosened, hence the force can escape, and the load to be applied to the erecting operation mechanism 120 can be decreased. Thus, even when a certain external force is applied to the movable member 96 exposed to the outside of the operation section 22, the wire 126 is loosened and hence the force can escape, thereby decreasing the load to be applied to the erecting operation mechanism 120.

Figure 15:
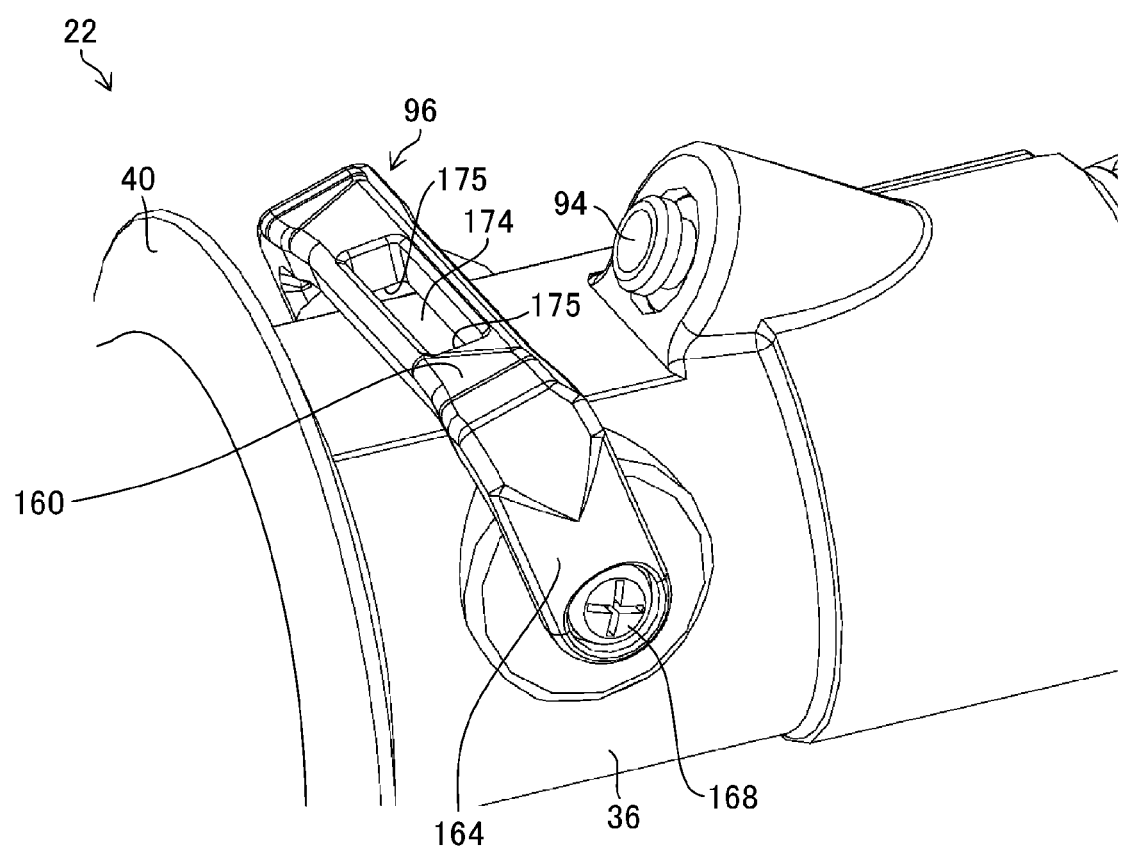
FIG. 15 is a perspective view of an extension part illustrating a lead-in port and a movable member.
Figure 16:
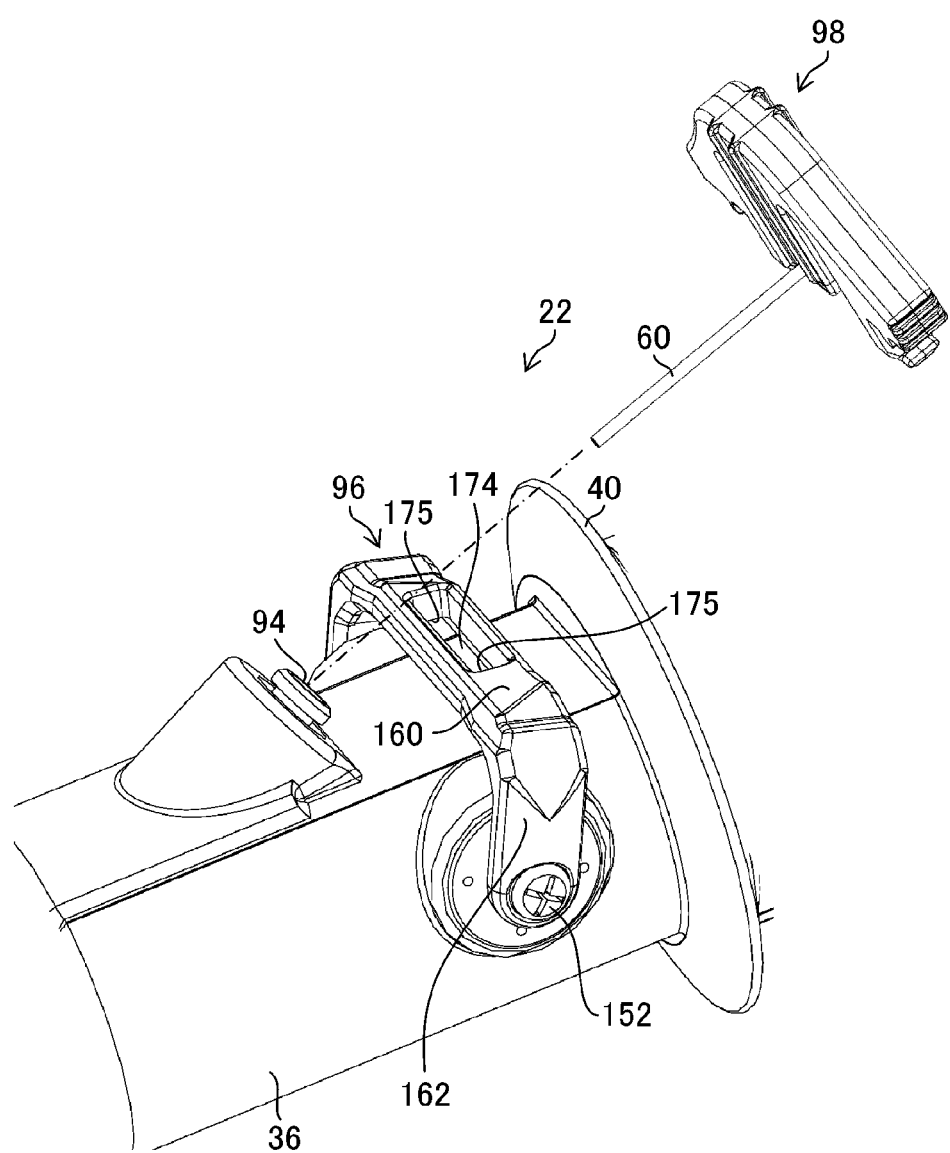
FIG. 16 is an explanatory diagram when a wire is inserted from the lead-in port while an engagement member is at the head.

The shape of the movable member 96 is described here. As illustrated in FIGS. 15 and 16 (described later), the movable member 96 includes a flat-plate-shaped beam portion 160, and the leg portions 162 and 164 provided on both ends of the beam portion 160. The movable member 96 is formed in a U-like shape as a whole. Referring to FIGS. 9 and 10, the drive shaft 152 provided on the leg portion 162 side is rotatably supported by the exterior case (not illustrated) of the operation section 22 via an O-ring 166, and a driven shaft 168 provided on the leg portion 164 side is rotatably supported by the exterior case (not illustrated) via an O-ring (not illustrated). With the O-ring 166 and the other O-ring, the operation section 22 is held watertight.

The rotation axes of the drive shaft 152 and the driven shaft 168 of the movable member 96 are set in a direction (X(+)-X(−) direction) perpendicular to the axial direction of the wire 60. That is, since the movable member 96 is rotatably provided while the direction perpendicular to the axial direction of the wire 60 serves as the rotation axis, the wire 60 can be smoothly pushed/pulled.

Next, a coupling structure 170 according to a first embodiment that couples the proximal end of the wire 60 to the movable member 96 is described with reference to FIGS. 11 to 15.

Figure 11:
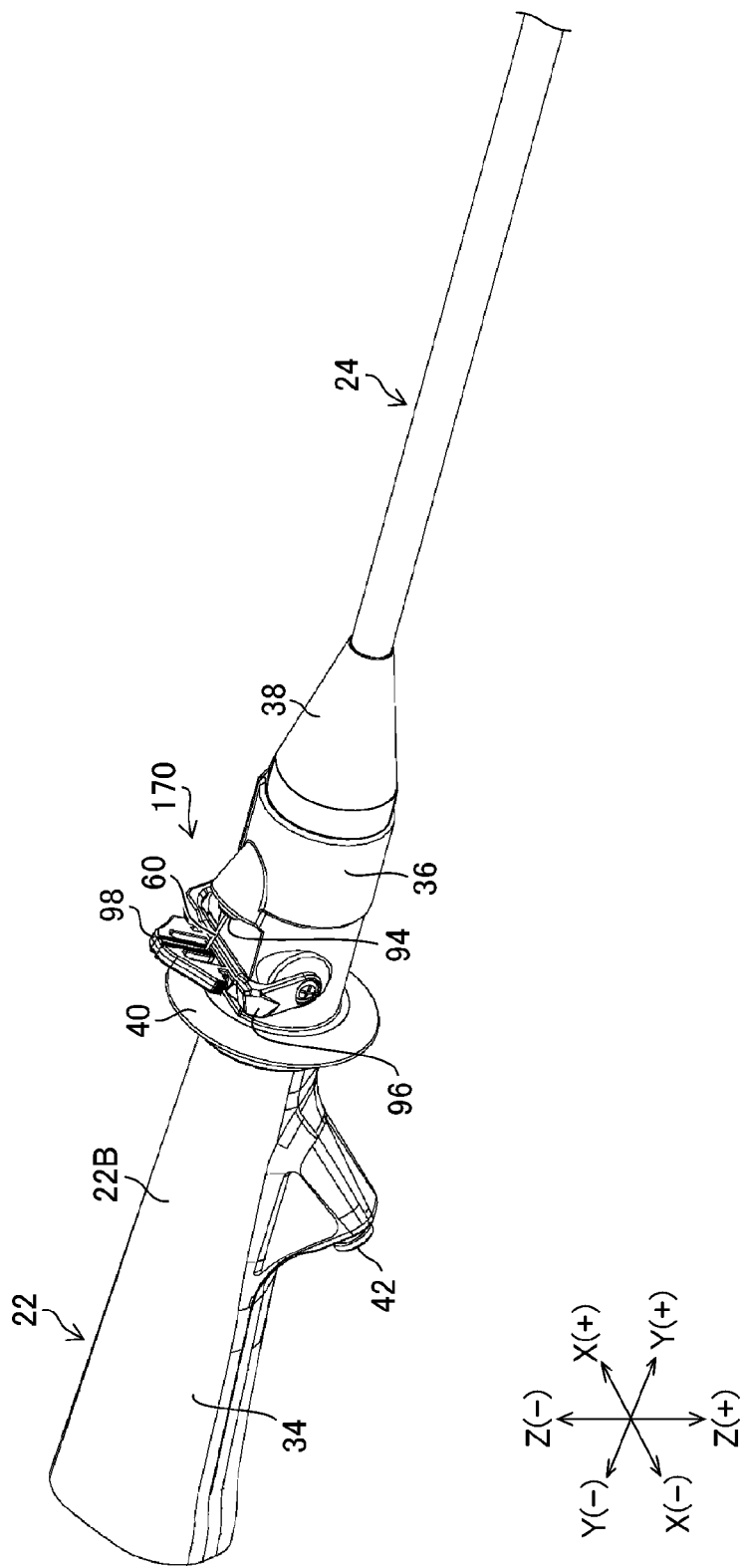
FIG. 11 is a perspective view of a coupling structure according to a first embodiment.
Figure 12:
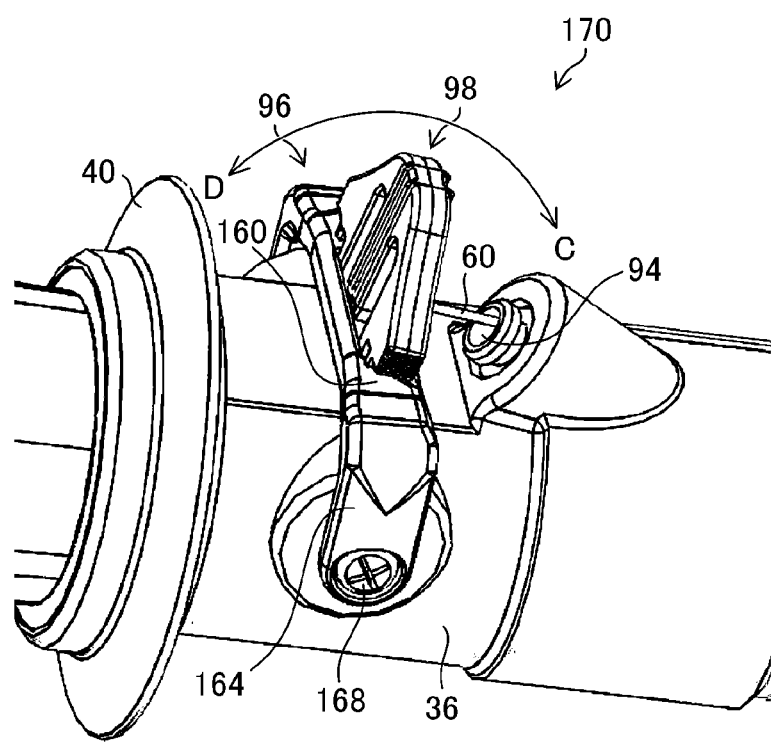
FIG. 12 is a perspective view when the coupling structure illustrated in FIG. 11 is viewed from the left.

FIG. 11 is a perspective view when the coupling structure 170 is viewed from the other side surface 22B of the operation section 22. FIG. 12 is a perspective view when the coupling structure 170 illustrated in FIG. 11 is viewed from the left.

Figure 13:
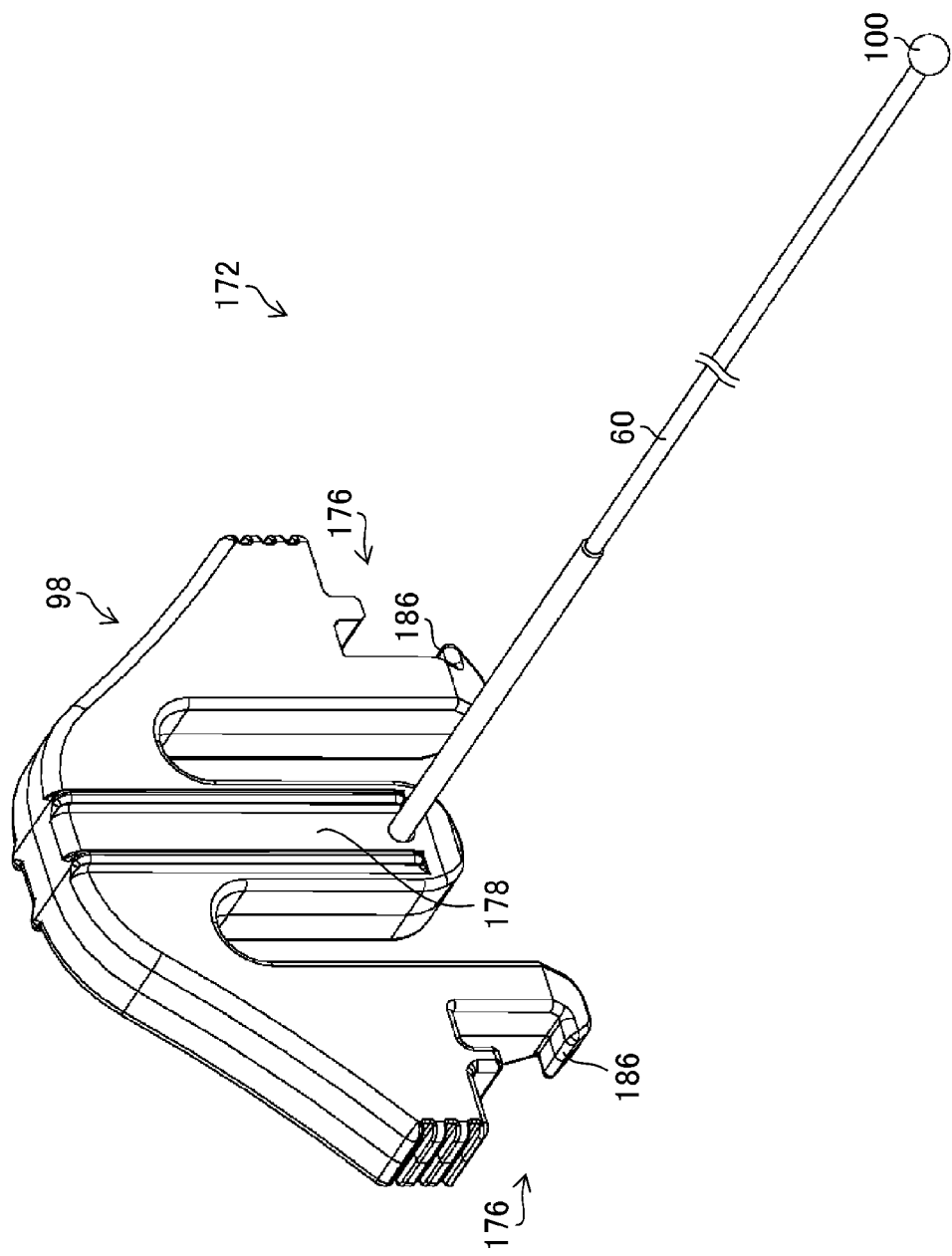
FIG. 13 is a perspective view of a wire assembly.
Figure 14:
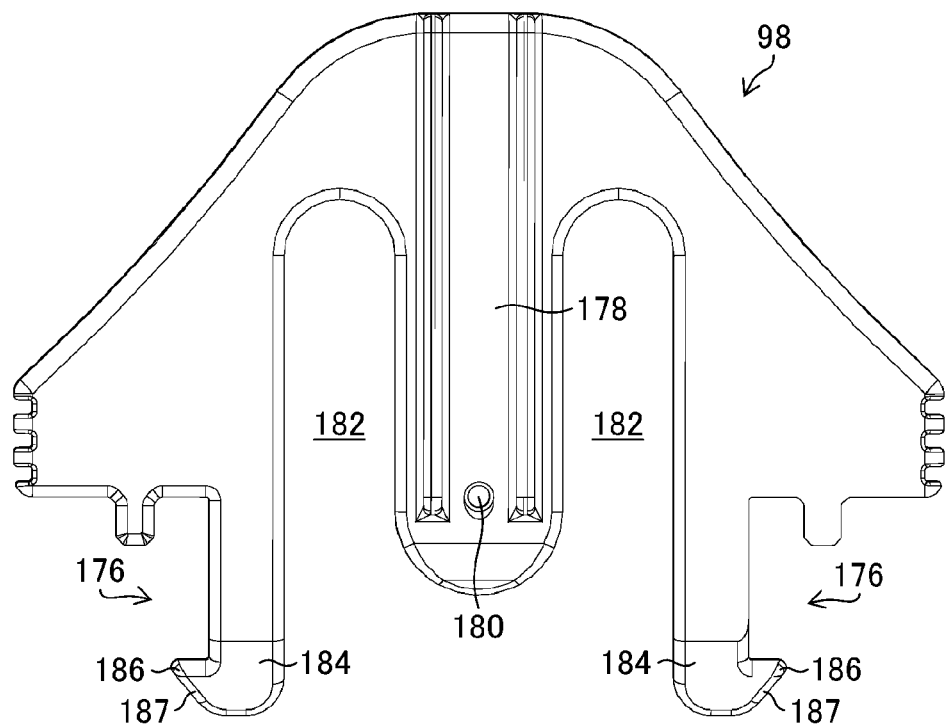
FIG. 14 is a front view of an attachment member.

FIG. 13 is a perspective view of a wire assembly 172 including the wire 60 and the attachment member 98 provided at the proximal end of the wire 60. FIG. 14 is a front view of the attachment member 98. FIG. 15 is a perspective view of the extension part 36 illustrating the lead-in port 94 and the movable member 96.

FIGS. 11 to 15 described above are explanatory diagrams for illustrating the coupling structure 170. FIGS. 11 and 12 illustrate a state in which the proximal end of the wire 60 and the movable member 96 are coupled by the coupling structure 170. FIGS. 13 to 15 illustrate the attachment member 98 and the movable member 96 that configure the coupling structure 170.

As illustrated in FIG. 15, the movable member 96 includes an engagement hole 174 with which the attachment member 98 is engaged in an attachable/detachable manner by a one-touch operation. The engagement hole 174 is formed along the longitudinal direction of the beam portion 160 of the movable member 96, and is configured of a through hole extending through the front and back surfaces of the beam portion 160. A pair of engagement portions 176 (see FIG. 14) of the attachment member 98 are engaged with the engagement hole 174 in an attachable/detachable manner by a one-touch operation. That is, the attachment member 98 is engaged with the movable member 96 in an attachable/detachable manner by a one-touch operation. Accordingly, with the coupling structure 170 according to the first embodiment, the proximal end of the wire 60 and the movable member 96 are coupled to each other outside the operation section 22. Alternatively, the engagement hole 174 may be a recessed non-through hole not extending through the front and back surfaces of the beam portion 160.

In this specification, being "engaged in an attachable/detachable manner by a one-touch operation" represents that a movement for attachment of the attachment member 98 to the movable member 96 and a movement for detachment of the attachment member 98 from the movable member 96 can be performed only by the movement of the attachment member 98 relative to the movable member 96 without using another fixing tool (for example, a screw, a bolt, or a nut). This is applied to other embodiments (described later).

The attachment member 98 illustrated in FIG. 14 is a substantially triangular plate-shaped body, and has a hole portion 180 at a core portion 178 of a center portion of the attachment member 98. The proximal end of the wire 60 is coupled to the hole portion 180. The engagement portions 176 of the attachment member 98 are provided on both sides of the core portion 178 with slit-shaped cut portions 182 interposed between the engagement portions 176 and the core portion 178. The engagement portions 176 are provided with a pair of elastic deformation portions 184 that are elastically deformed and engaged with the engagement hole 174. The elastic deformation portions 184 have a pair of claw portions 186 at edge portions 175 (see FIGS. 15 and 16) on both sides in the longitudinal direction of the engagement hole 174. The pair of claw portions 186 are displaced in directions to move toward each other by elastic deformation of the pair of elastic deformation portions 184 when the engagement portions 176 are engaged with or disengaged from the engagement hole 174.

Next, the coupling procedure of the proximal end of the wire 60 and the movable member 96 to each other with the coupling structure 170 according to the first embodiment is described with reference to FIGS. 16 to 18.

Before the proximal end of the wire 60 and the movable member 96 are coupled to each other, the distal end of the wire 60 is coupled to the erecting base 30.

FIG. 16 illustrates a state in which the wire 60 is inserted from the lead-in port 94 while the engagement member 100 (see FIG. 13) is at the head. With the insertion operation of the wire 60, the distal end of the wire 60 is coupled to the erecting base 30.

That is, in the state in which the erecting base 30 is located at the erecting position (see FIG. 3), referring to FIG. 16, when the wire 60 is led in from the lead-in port 94 while the engagement member 100 is at the head, the engagement member 100 is inserted through the wire channel 62 (see FIG. 2) and is led out to the outside from the lead-out port 74. The engagement member 100 is guided by the engagement guide portion 106 in FIG. 3 toward the opening 104 of the housing groove 102 of the erecting base 30 through the ongoing lead-in operation of the wire 60, and is engaged with the housing groove 102 from the opening 104. Accordingly, the distal end of the wire 60 is coupled to the erecting base 30.

Figure 17:
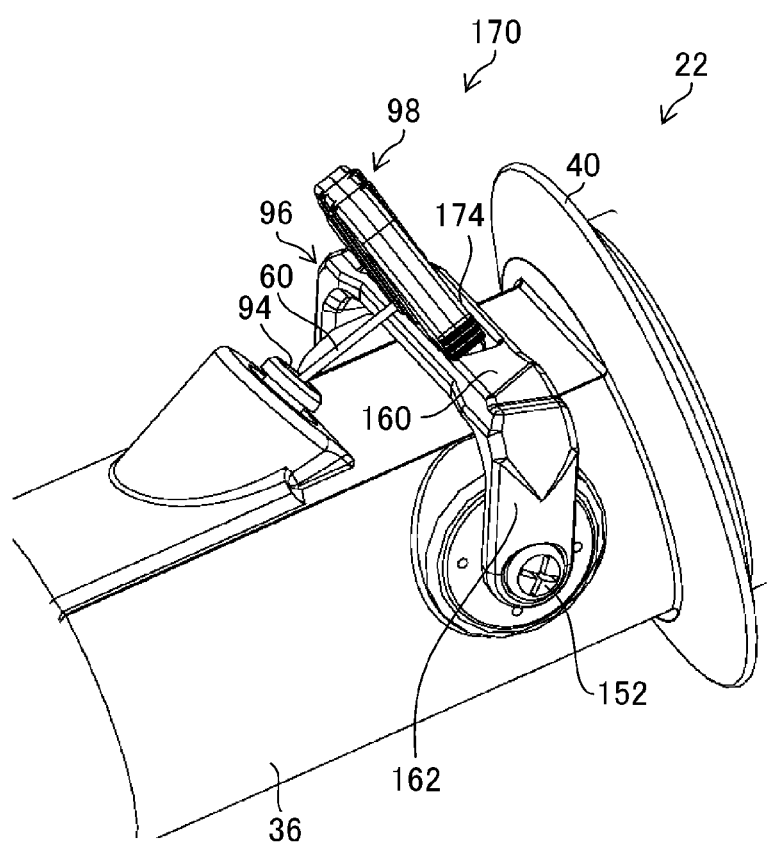
FIG. 17 is an explanatory diagram of the attachment member in a state in which the distal end of the wire is coupled to the erecting base.
Figure 18:
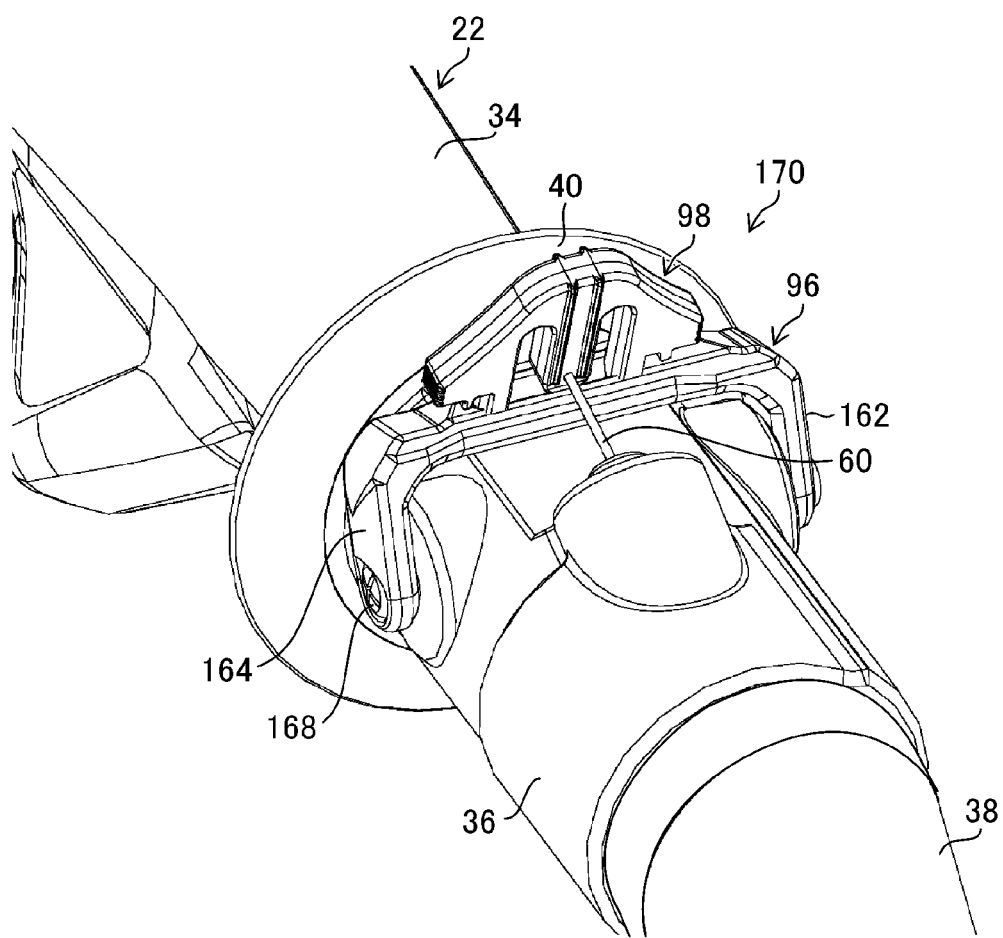
FIG. 18 is an explanatory diagram when the attachment member is coupled to the movable member.

FIG. 17 illustrates the state of the attachment member 98 in a state in which the distal end of the wire 60 is coupled to the erecting base 30. In this state, tapered portions 187 located below the claw portions 186 are brought into contact with edges on both sides of the engagement hole 174 and are pushed into the engagement hole 174. With this movement, the distance between the claw portions 186 is decreased, the claw portions 186 are latched to the edge portions 175 on both sides of the engagement hole 174, and the attachment member 98 is coupled to the movable member 96 referring to the coupling diagram of FIG. 18.

Accordingly, with the coupling structure 170 according to the first embodiment, the movement for attachment of the attachment member 98 to the movable member 96 can be performed only by the movement of the attachment member 98 relative to the movable member 96. That is, with the coupling structure 170 according to the first embodiment, the attachment member 98 can be engaged with the movable member 96 by a one-touch operation.

When the attachment member 98 is mounted at the movable member 96, the pair of engagement portions 176 of the attachment member 98 can be pinched with fingers of a hand to narrow the distance between the claw portions 186 to be smaller than the dimension in the longitudinal direction of the engagement hole 174. That is, the pair of elastic deformation portions 184 are displaced in directions to move toward each other by elastic deformation. After the claw portions 186 are inserted into the engagement hole 174, by relaxing the force of the fingers of the hand to expand the distance between the claw portions 186, the claw portions 186 are latched to the edge portions 175 on both sides of the engagement hole 174. Accordingly, the attachment member 98 can be engaged with the movable member 96 by a one-touch operation.

Then, when the erecting operation lever 20 in FIG. 1 is operated, as illustrated in the movement explanatory diagram of the movable member 96 in FIG. 12, the movable member 96 moves in a direction of arrow C or arrow D. Then, in association with the movement of the movable member 96, the wire 60 is operated to be pushed/pulled by the movable member 96 via the attachment member 98. Accordingly, the erecting base 30 is rotated between the erecting position and the lying position.

According to the embodiment, the engagement hole 174 is formed in the movable member 96 and the engagement portions 176 are formed at the attachment member 98. However, the engagement portions 176 may be formed at the movable member 96 and the engagement hole 174 may be formed in the attachment member 98. That is, the engagement hole 174 may be provided in one of the movable member 96 and the attachment member 98, and the engagement portions 176 that are engaged with the engagement hole 174 in an attachable/detachable manner by a one-touch operation may be provided at the other one. The claw portions 186 may not be provided on the sides in the longitudinal direction of the beam portion 160 of the movable member 96, and may be provided on the sides in the transverse direction of the beam portion 160. The engagement hole 174 may be two engagement holes formed to be spaced apart in the longitudinal direction of the beam portion 160.

The endoscope 10 is used for one of various inspections or one of various treatments. Thereafter, when the endoscope 10 is washed, the following works are performed.

First, the cap 76 illustrated in FIG. 2 is removed from the distal end member 28. Then, the engagement portions 176 of the attachment member 98 are removed from the engagement hole 174 (see FIG. 15) of the movable member 96, and the wire 60 is removed from the movable member 96. Then, the wire 60 is operated to be pushed from the lead-in port 94 of the extension part 36 to cause the erecting base 30 to be located at the lying position in FIG. 2 from the erecting position in FIG. 3. Then, by further operating the wire 60 to be pushed, the engagement member 100 is detached to the outside of the opening 104 from the inside of the housing groove 102. With the works, the distal end of the wire 60 is removed from the erecting base 30. Then, the wire 60 is pulled out from the lead-in port 94, and the wire channel 62 is made empty. Then, the distal end member 28, the erecting base 30, and the wire channel 62 of the wire 60 are washed.

In the work of removing the distal end of the wire 60 from the erecting base 30, in the coupling structure 170 according to the first embodiment, since the attachment member 98 is coupled to the movable member 96 outside the operation section 22, the attachment member 98 can be easily removed from the movable member 96. Specifically, the pair of engagement portions 176 of the attachment member 98 are pinched with fingers of a hand to narrow the distance between the claw portions 186 to be smaller than the dimension in the longitudinal direction of the engagement hole 174. Then, the claw portions 186 are pulled out from the engagement hole 174. Accordingly, the attachment member 98 is detached from the movable member 96 by a one-touch operation.

Accordingly, with the coupling structure 170 according to the first embodiment, the movement for detachment of the attachment member 98 from the movable member 96 can be performed only by the movement of the attachment member 98 relative to the movable member 96.

As described above, with the coupling structure 170 according to the first embodiment, after the distal end of the wire 60 is coupled to the erecting base 30, merely by engaging the engagement portions 176 of the attachment member 98 with the engagement hole 174 of the movable member 96 outside the operation section 22, the proximal end of the wire 60 can be coupled to the movable member 96. When the endoscope 10 is washed, to remove the proximal end of the wire 60 from the movable member 96, merely by detaching the attachment member 98 from the engagement hole 174 of the movable member 96 outside the operation section 22, the proximal end of the wire 60 can be removed from the movable member 96.

Thus, with the coupling structure 170 according to the first embodiment, compared with the endoscope of JP1994-315458A (JP-H6-315458A) that performs the attachment/detachment work of the proximal end of the wire to/from the connecting tool in the operation section, the attachment/detachment operation of the proximal end of the wire 60 to/from the movable member 96 can be easily performed.

With the coupling structure 170 according to the first embodiment, the operation section 22 includes the extension part 36 extending from the holding part 34 toward the distal end side, and the erecting operation mechanism 120 having the movable member 96 is provided in the extension part 36. Accordingly, with the coupling structure 170 according to the first embodiment, compared with the endoscope of JP1994-315458A (JP-H6-315458A) including the connecting tool of the erecting operation mechanism in the grip part (the holding part), an increase in size of the holding part 34 can be prevented.

Moreover, the movable member 96 is arranged to be exposed to the outside of the extension part 36. Accordingly, the extension part 36 does not need to have the arrangement space for the movable member 96. The extension part 36 can be decreased in size.

Meanwhile, in a configuration in which the operation section 22 does not include the extension part 36 unlike the embodiment, the movable member 96 may be provided at the holding part 34. In this case, since the holding part 34 is a part that is held by an operator, if the operator who holds the holding part 34 touches the movable member 96 with hand, the movable member 96 may have an unintentional movement. Hence, the operator who holds the holding part 34 needs to operate the endoscope 10 while paying attention not to touch the movable member 96 with hand.

In contrast, in the embodiment, the movable member 96 is arranged at the extension part 36 extending from the holding part 34 toward the distal end side. The touching on the movable member 96 by the operator who holds the holding part 34 with hand can be prevented from occurring. Accordingly, in the embodiment, a situation in which the hand holding the holding part 34 touches the movable member 96 and causes an unintentional movement can be prevented from occurring. Consequently, compared with the configuration in which the movable member 96 is arranged at the holding part 34, ease of operation of the endoscope 10 can be increased.

In the above-described embodiment, the wire 60 is pulled out from the lead-in port 94. However, the wire 60 may be pulled out from the lead-out port 74 of the distal end member 28. In this case, by removing the attachment member 98 from the proximal end of the wire 60 before the wire 60 is pulled out, the wire 60 can be pulled out from the lead-out port 74.

FIG. 19 is a perspective view illustrating a modification of the coupling structure 170 according to the first embodiment illustrated in FIGS. 11 to 18.

A coupling structure 170A according to a modification illustrated in FIG. 19 is described with the same reference signs applied to the same or similar members as or to those of the coupling structure 170 illustrated in FIGS. 11 to 18.

An engagement hole 174A formed in the movable member 96 is a circular through hole. An engagement portion 176A of an attachment member 98A has a tubular portion 177 that is fitted into the engagement hole 174A. An elastic deformation portion of the attachment member 98A is configured of a slotted portion 184A provided at a distal end portion of the tubular portion 177. A claw portion 186A is formed at the outer peripheral surface of the slotted portion 184A.

Figure 20:
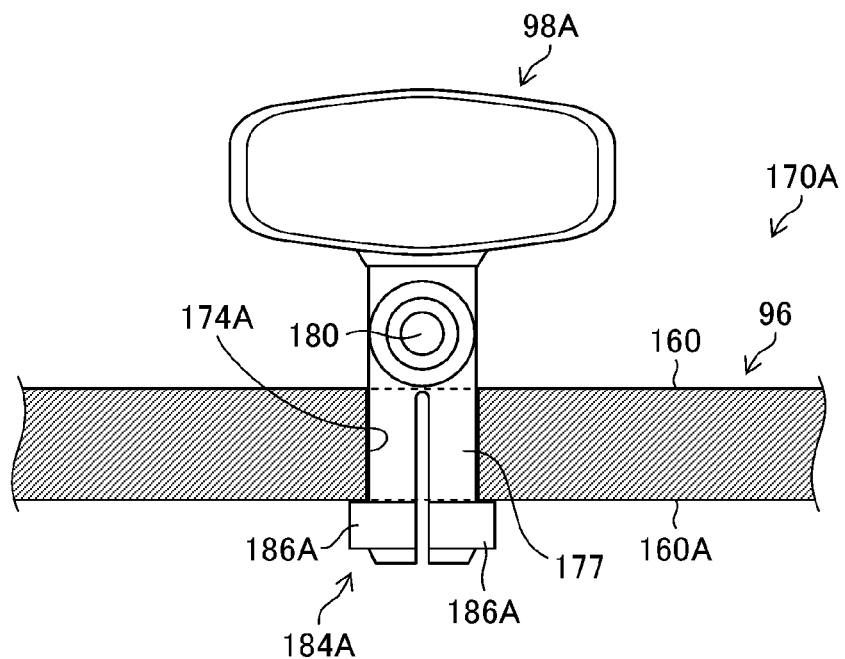
FIG. 20 is a main-part sectional view of the coupling structure illustrated in FIG. 19.

With the thus configured coupling structure 170A, when the slotted portion 184A of the tubular portion 177 is fitted into the engagement hole 174A, the diameter of the slotted portion 184A is decreased by elastic deformation. Accordingly, after the slotted portion 184A is passing through the engagement hole 174A and then the slotted portion 184A has passed through the engagement hole 174A, the diameter of the slotted portion 184A is restored to the original diameter. Thus, referring to the sectional view of the coupling structure 170A illustrated in FIG. 20, the claw portion 186A of the slotted portion 184A is engaged with a back surface 160A of the beam portion 160 of the movable member 96. The attachment member 98A is engaged with the movable member 96 by a one-touch operation.

Even with the coupling structure 170A, the attachment/detachment work of the attachment member 98A to/from the movable member 96 is performed outside the operation section 22 similarly to the coupling structure 170. The attachment work is of merely inserting the engagement portion 176A into the engagement hole 174A. With the attachment work, the proximal end of the wire 60 can be easily coupled to the movable member 96 via the attachment member 98A.

When the attachment member 98A is removed from the movable member 96, the slotted portion 184A is pinched with fingers to decrease the diameter of the slotted portion 184A. Then, the slotted portion 184A is pulled out from the engagement hole 174A.

Accordingly, even with the coupling structure 170A according to the modification, the movement for attachment of the attachment member 98A to the movable member 96 and the movement for detachment of the attachment member 98A from the movable member 96 can be performed only by the movement of the attachment member 98A relative to the movable member 96 similarly to the coupling structure 170. That is, with the coupling structure 170A, the attachment member 98A is engaged with the movable member 96 in an attachable/detachable manner by a one-touch operation.

Figure 21:
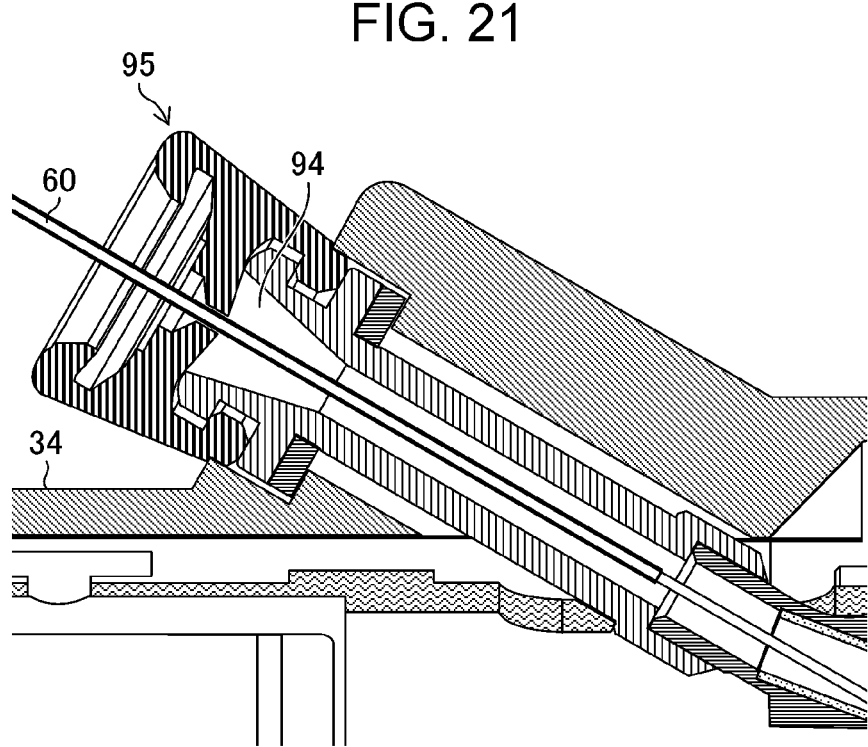
FIG. 21 is a sectional view illustrating a state in which a valve body is mounted at the lead-in port.

FIG. 21 is a sectional view illustrating a state in which a valve body 95 is mounted at the lead-in port 94. In the embodiment, since the proximal end of the wire 60 is arranged outside the lead-in port 94, the valve body 95 is preferably mounted at the lead-in port 94. Accordingly, liquid in a body cavity which flows backward from the lead-out port 74 of the distal end member 28 via the wire channel 62 can be prevented from leaking to the outside from the lead-in port 94.

Figure 24:
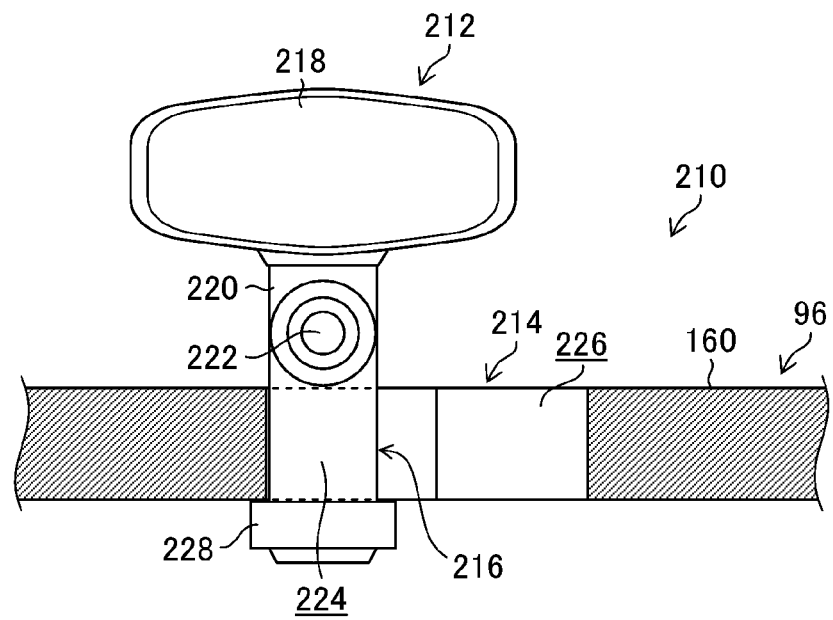
FIG. 24 is a main-part sectional view of the coupling structure illustrated in FIG. 22.

Next, a coupling structure 210 according to a second embodiment is described with reference to FIGS. 22 to 24.

Figure 22:
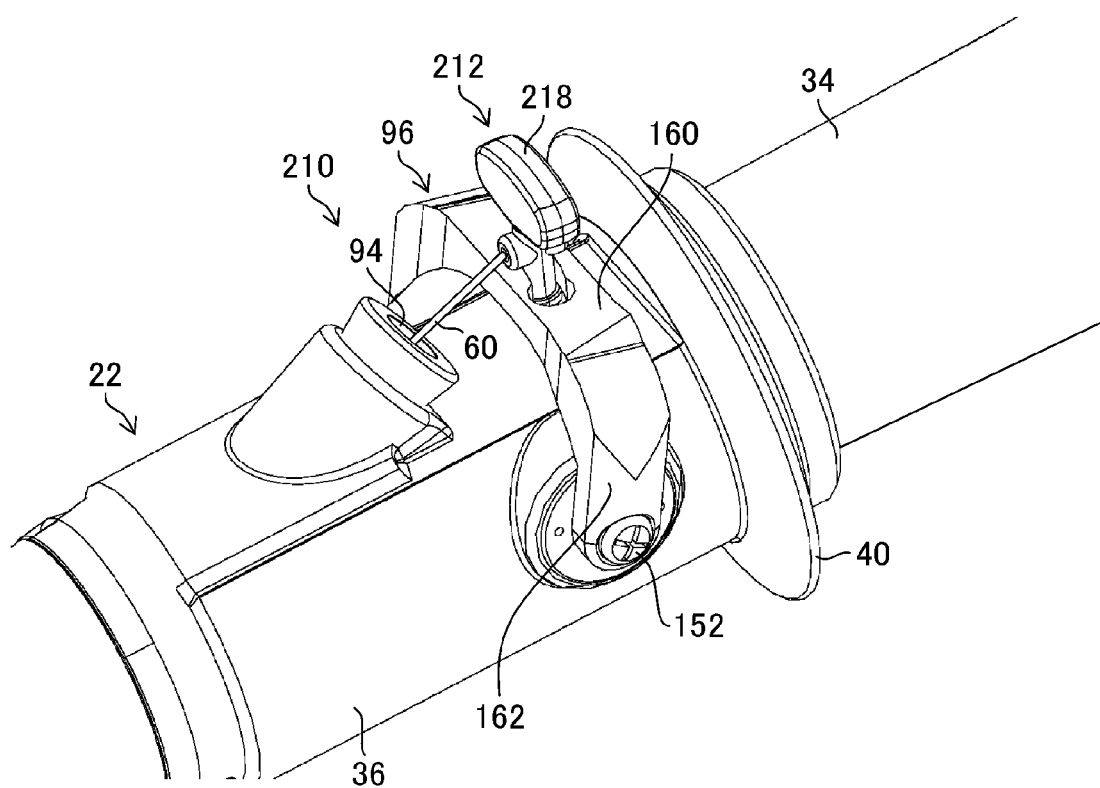
FIG. 22 is a perspective view of a coupling structure according to a second embodiment.

FIG. 22 is a perspective view of the coupling structure 210. FIG. 23 is an assembly perspective view of the coupling structure 210. FIG. 24 is a main-part sectional view of the coupling structure 210. The coupling structure 210 is described with the same reference signs applied to the same or similar members as or to those of the coupling structure 170 illustrated in FIGS. 11 to 18.

The coupling structure 210 is configured of a movable member 96 and an attachment member 212.

Referring to FIG. 23, an engagement hole 214 is provided in a beam portion 160 of the movable member 96, and an engagement portion 216 that is engaged with the engagement hole 214 in an attachable/detachable manner by a one-touch operation is provided at the attachment member 212. The attachment member 212 is configured of a pinch portion 218 and a shaft portion 220 configuring the engagement portion 216. The proximal end of the wire 60 is coupled to a hole portion 222 formed in the shaft portion 220.

Figure 25:
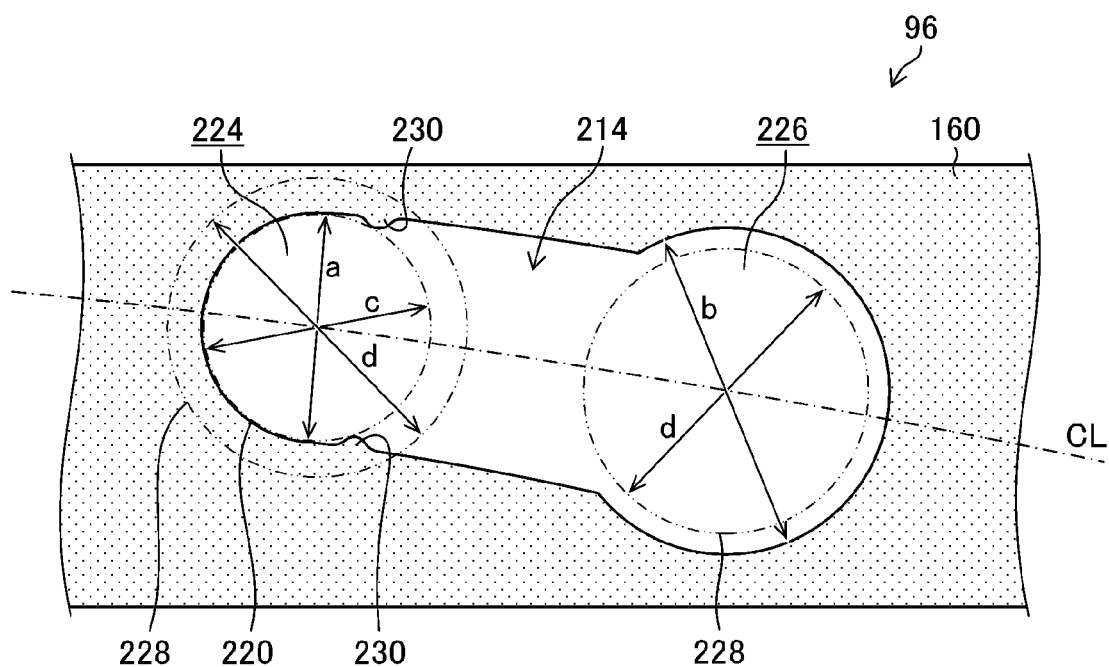
FIG. 25 is a plan view illustrating the size of an engagement portion with respect to an engagement hole.

The shape of the engagement hole 214 is described here. FIG. 25 is a plan view of the engagement hole 214, and illustrating a state in which the shape of the engagement portion 216 is superposed on the shape of the engagement hole 214.

The engagement hole 214 has a small width portion 224 having a diameter a and a large width portion 226 having a diameter b that is larger than the diameter a. In the embodiment, a first width according to the present invention is described as the diameter a, and a second width according to the present invention is described as the diameter b. As illustrated in FIG. 25, a line CL connecting the center of the small width portion 224 and the center of the large width portion 226 is a curved line. The line CL defines a substantial arc centered on the lead-in port 94 (not illustrated). The arrangement of the small width portion 224 and the large width portion 226 makes an operation easy when the attachment member 212 is engaged with the engagement hole 214. This will be described later.

The engagement portion 216 of the attachment member 212 illustrated in FIG. 23 has the shaft portion 220 having an outside diameter c that is equal to or smaller than the diameter a in FIG. 25, and a large diameter portion 228 provided at the distal end of the shaft portion 220. The large diameter portion 228 has an outside diameter d that is larger than the diameter a and smaller than the diameter b. The large diameter portion 228 functions as a fall prevention portion that restricts detachment of the shaft portion 220 from the small width portion 224 in the axial direction of the shaft portion 220. To stably hold the shaft portion 220, the difference between the diameter a and the outside diameter c is preferably small.

The engagement operation is described. Since the large width portion 226 of the engagement hole 214 is larger than the large diameter portion 228, the engagement portion 216 of the attachment member 212 can be easily inserted into the engagement hole 214. Then, the attachment member 212 is slid from the large width portion 226 to the small width portion 224. At this time, as illustrated in FIG. 22, the attachment member 212 is fixed to the wire 60, and hence the attachment member 212 moves on a substantially arc-shaped locus centered on the lead-in port 94. Since the small width portion 224 and the large width portion 226 are arranged in a substantially arc form as described above, the attachment member 212 can smoothly slide between the small width portion 224 and the large width portion 226. Furthermore, when the attachment member 212 is located at the small width portion 224, a tension can be applied to the wire 60.

The engagement hole 214 has a frictional resistance portion 230 between the small width portion 224 and the large width portion 226. The frictional resistance portion 230 is provided at an opening entrance portion of the small width portion 224. The frictional resistance portion 230 can restrict unintentional sliding of the shaft portion 220 inserted into the small width portion 224, from the small width portion 224 to the large width portion 226. The frictional resistance portion 230 is formed to protrude from each of mutually facing wall surfaces of the engagement hole 214.

Even with the thus configured coupling structure 210, the attachment/detachment work of the attachment member 212 to/from the movable member 96 is performed outside the operation section 22 similarly to the coupling structure 170. The attachment work is of merely inserting the engagement portion 216 into the large width portion 226 of the engagement hole 214, sliding the engagement portion 216 toward the small width portion 224, and engaging the engagement portion 216 with the small width portion 224. Accordingly, the attachment member 212 can be engaged with the movable member 96 by a one-touch operation. With the attachment work, the proximal end of the wire 60 can be easily coupled to the movable member 96 via the attachment member 212.

When the engagement portion 216 is slid from the large width portion 226 toward the small width portion 224, the shaft portion 220 comes into contact with the frictional resistance portion 230. However, the engagement portion 216 can be properly engaged with the small width portion 224 by the force of sliding the engagement portion 216.

Moreover, in a state in which the engagement portion 216 is engaged with the small width portion 224, the large diameter portion 228 prevents the shaft portion 220 from being detached from the small width portion 224 in the axial direction of the shaft portion 220. Furthermore, since the shaft portion 220 comes into contact with the frictional resistance portion 230, sliding of the engagement portion 216 from the small width portion 224 to the large width portion 226 is restricted. Accordingly, the attachment member 212 can be reliably coupled to the movable member 96.

When the endoscope 10 is washed, to remove the attachment member 212 from the movable member 96, the engagement portion 216 of the attachment member 212 is slid from the small width portion 224 to the large width portion 226, and the engagement portion 216 is pulled out from the large width portion 226. Accordingly, the attachment member 212 is detached from the movable member 96 by a one-touch operation.

Thus, with the coupling structure 210 according to the second embodiment, compared with the endoscope of JP1994-315458A (JP-H6-315458A), the attachment/detachment operation of the proximal end of the wire 60 to/from the movable member 96 can be easily performed.

Moreover, with the coupling structure 210 according to the second embodiment, since the erecting operation mechanism having the movable member 96 is provided in the extension part 36, compared with the endoscope of JP1994-315458A (JP-H6-315458A) including the connecting tool of the erecting operation mechanism in the holding part, an increase in size of the holding part 34 can be prevented. Moreover, the movable member 96 is arranged to be exposed to the outside of the extension part 36. Accordingly, the extension part 36 does not need to have the arrangement space for the movable member 96. The extension part 36 can be decreased in size.

In FIG. 25, the engagement hole 214 including the frictional resistance portion 230 is illustrated as an example; however, the engagement hole 214 may not include the frictional resistance portion 230.

Next, a coupling structure 232 according to a third embodiment is described with reference to FIGS. 26 and 27.

FIG. 26 is an assembly perspective view of the coupling structure 232. FIG. 27 is a plan view of an engagement hole 214 formed in a movable member 96, and illustrating a state in which the shape of an engagement portion 236 of an attachment member 234 is superposed on the shape of the engagement hole 214. The coupling structure 232 is described with the same reference signs applied to the same or similar members as or to those of the coupling structure 210 illustrated in FIGS. 22 to 25.

Figure 27:
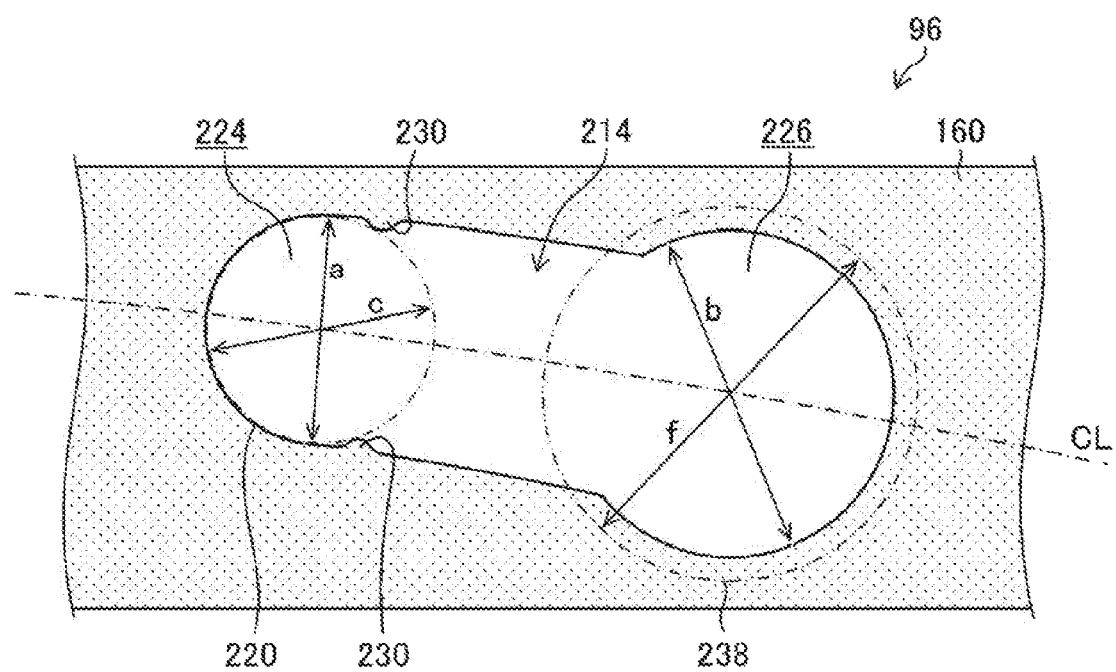
FIG. 27 is a plan view of an engagement hole illustrating the size of an engagement portion with respect to the engagement hole.

As illustrated in FIG. 27, the engagement hole 214 has a small width portion 224 having a diameter a and a large width portion 226 having a diameter b that is larger than the diameter a. The small width portion 224 and the large width portion 226 have a positional relationship similar to that illustrated in FIG. 25.

The engagement portion 236 of the attachment member 234 illustrated in FIG. 26 has a shaft portion 220 having an outside diameter c that is equal to or smaller than the diameter a, and a large diameter portion 238 provided at the distal end of the shaft portion 220 and having an outside diameter f that is larger than the diameter b. A plurality of (for example, four) slotting grooves 237 (see FIG. 26) are formed in the large diameter portion 238. When the large diameter portion 238 is fitted into the large width portion 226, the large diameter portion 238 is elastically deformed by the plurality of slotting grooves 237 and the diameter of the large diameter portion 238 is decreased. To stably hold the shaft portion 220, the difference between the diameter a and the outside diameter c is preferably small.

Even with the thus configured coupling structure 232, the attachment/detachment work of the attachment member 234 to/from the movable member 96 is performed outside the operation section 22 similarly to the coupling structure 210. The attachment work is of first fitting the large diameter portion 238 into the large width portion 226 of the engagement hole 214. At this time, the large diameter portion 238 is elastically deformed by the plurality of slotting grooves 237 and the diameter of the large diameter portion 238 is decreased. Accordingly, after the large diameter portion 238 is passing through the large width portion 226 and then the large diameter portion 238 has passed through the large width portion 226, the diameter of the large diameter portion 238 is restored to the original diameter. Thus, the large diameter portion 238 is engaged with a back surface 160A of a beam portion 160 of the movable member 96. The attachment member 234 is prevented from coming out from the movable member 96.

Then, the engagement portion 236 is slid toward the small width portion 224, and the engagement portion 236 is engaged with the small width portion 224. Accordingly, the attachment member 234 can be engaged with the movable member 96 by a one-touch operation. With the attachment work, the proximal end of the wire 60 can be easily coupled to the movable member 96 via the attachment member 234.

Moreover, in a state in which the engagement portion 236 is engaged with the small width portion 224, the large diameter portion 238 prevents the shaft portion 220 from being detached from the small width portion 224 in the axial direction of the shaft portion 220. Furthermore, since the shaft portion 220 comes into contact with the frictional resistance portion 230, sliding of the engagement portion 236 from the small width portion 224 to the large width portion 226 is restricted. Accordingly, the attachment member 234 can be reliably coupled to the movable member 96.

When the endoscope 10 is washed, to remove the attachment member 234 from the movable member 96, the engagement portion 236 of the attachment member 234 is slid from the small width portion 224 to the large width portion 226, then the large diameter portion 238 is pinched with fingers to decrease the diameter of the large diameter portion 238, and the large diameter portion 238 is pulled out from the large width portion 226. Accordingly, the attachment member 234 is detached from the movable member 96 by a one-touch operation.

Thus, with the coupling structure 232 according to the third embodiment, compared with the endoscope of JP1994-315458A (JP-H6-315458A), the attachment/detachment operation of the proximal end of the wire 60 to/from the movable member 96 can be easily performed.

In FIG. 27, the engagement hole 214 including the frictional resistance portion 230 is illustrated as an example; however, the engagement hole 214 may not include the frictional resistance portion 230.

Next, a coupling structure 240 according to a fourth embodiment is described with reference to FIGS. 28 and 29.

Figure 28:
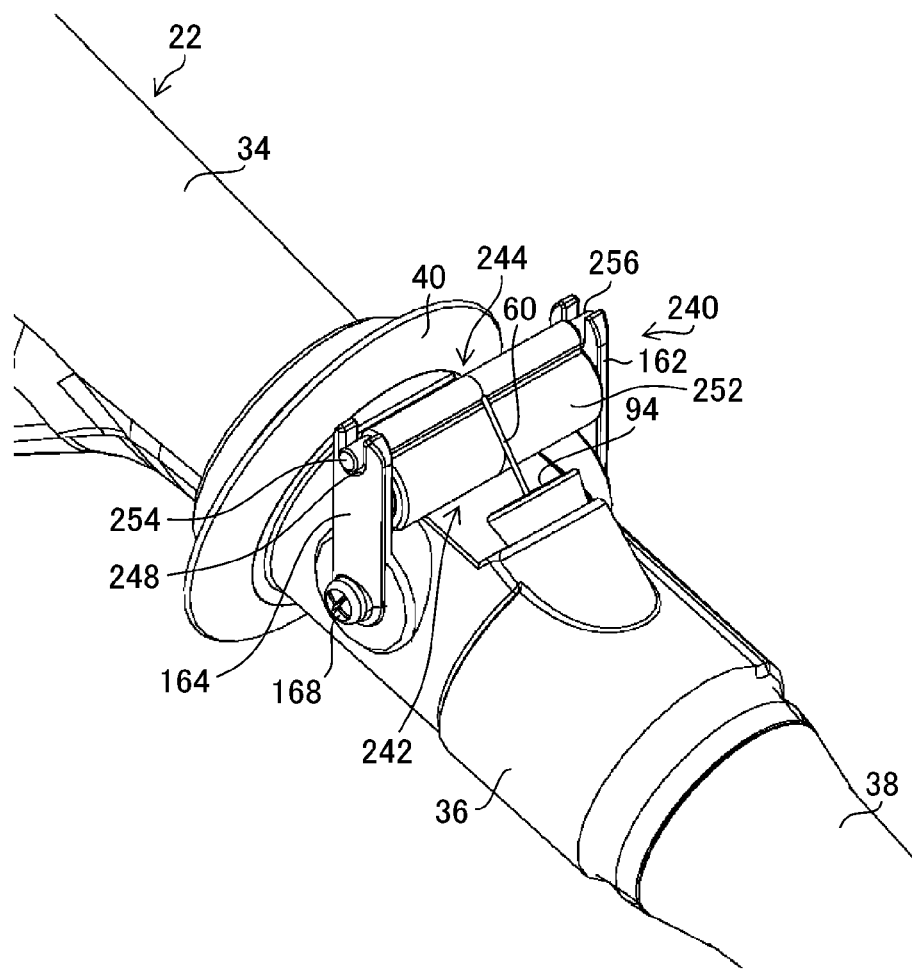
FIG. 28 is a perspective view of a coupling structure according to a fourth embodiment.
Figure 29:
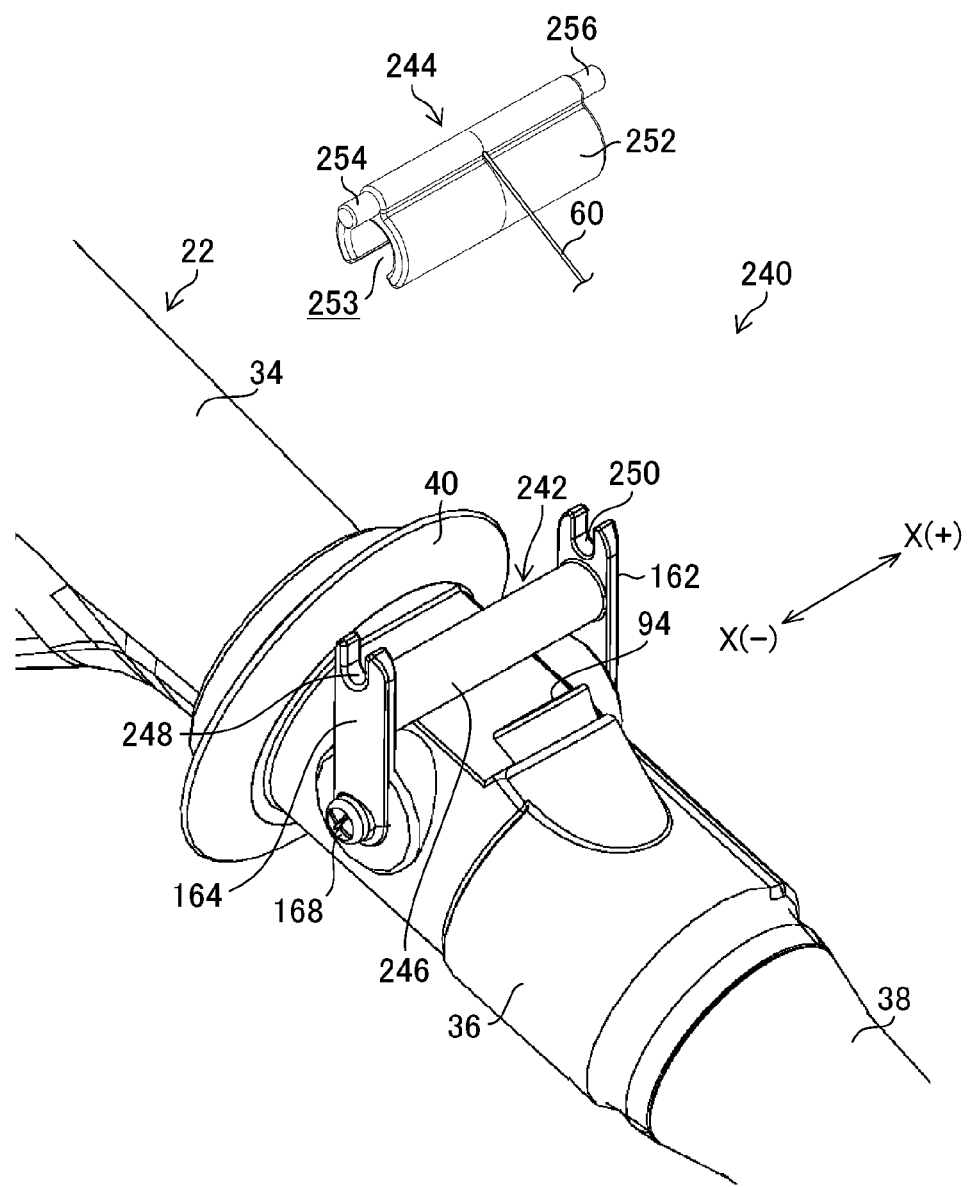
FIG. 29 is an assembly perspective view of the coupling structure illustrated in FIG. 28.

FIG. 28 is a perspective view of the coupling structure 240. FIG. 29 is an assembly perspective view of the coupling structure 240. The coupling structure 240 is described with the same reference signs applied to the same or similar members as or to those of the coupling structure 170 illustrated in FIGS. 11 to 18.

The coupling structure 240 is configured of a movable member 242 and an attachment member 244.

The movable member 242 is configured of a leg portion 162, a leg portion 164, and a cylindrical body 246 that couples the leg portion 162 and the leg portion 164 to each other. The cylindrical body 246 extends in a direction (X(+)-X(−) direction) perpendicular to the axial direction of the wire 60. Moreover, as illustrated in FIGS. 28 and 29, U-shaped grooves 248 and 250 configuring a rotation restriction stopper are formed in upper end portions of the leg portion 162 and the leg portion 164.

The proximal end of the wire 60 is coupled to the attachment member 244. The attachment member 244 is configured of a ring-shaped body 252 that is rotatably engaged with the outer periphery of the cylindrical body 246, and pins 254 and 256 that configure the rotation restriction stopper together with the grooves 248 and 250. The ring-shaped body 252 has a C-like shape in a section orthogonal to the longitudinal direction. By pressing a slit 253 that is formed in the ring-shaped body 252 in the longitudinal direction against the cylindrical body 246, the diameter of the ring-shaped body 252 is increased and is engaged with the cylindrical body 246 by a one-touch operation.

Even with the thus configured coupling structure 240, the attachment/detachment work of the attachment member 244 to/from the movable member 242 is performed outside the operation section 22 similarly to the coupling structures 170 and 210. The attachment work is of pressing the slit 253 of the ring-shaped body 252 of the attachment member 244 against the cylindrical body 246 of the movable member 242. With the work, the attachment member 244 is engaged with the movable member 242 by a one-touch operation. Accordingly, the proximal end of the wire 60 can be reliably coupled to the movable member 242 via the attachment member 244.

Moreover, when the ring-shaped body 252 is engaged with the cylindrical body 246, the pin 254 is engaged with the groove 248 and the pin 256 is engaged with the groove 250 simultaneously. When the wire 60 is operated to be pushed/pulled by the movable member 242, the ring-shaped body 252 can be prevented from being rotated relative to the cylindrical body 246. Accordingly, the pushing/pulling operation of the wire 60 can be smoothly performed.

When the endoscope 10 is washed, to remove the attachment member 244 from the movable member 242, the attachment member 244 is pulled in a direction in which the pins 254 and 256 are removed from the grooves 248 and 250, hence the ring-shaped body 252 is pushed by the cylindrical body 246, the diameter of the ring-shaped body 252 is increased, and the ring-shaped body 252 is removed from the cylindrical body 246. Accordingly, the attachment member 244 is detached from the movable member 242 by a one-touch operation.

Thus, with the coupling structure 240 according to the fourth embodiment, compared with the endoscope of JP1994-315458A (JP-H6-315458A), the attachment/detachment operation of the proximal end of the wire 60 to/from the movable member 242 can be easily performed.

Moreover, with the coupling structure 240 according to the fourth embodiment, since the erecting operation mechanism having the movable member 242 is provided in the extension part 36, compared with the endoscope of JP1994-315458A (JP-H6-315458A) including the connecting tool of the erecting operation mechanism in the holding part, an increase in size of the holding part 34 can be prevented. Moreover, the movable member 242 is arranged to be exposed to the outside of the extension part 36. Accordingly, the extension part 36 does not need to have the arrangement space for the movable member 242. The extension part 36 can be decreased in size.

In the above-described embodiment, the cylindrical body 246 is provided at the movable member 242, and the ring-shaped body 252 is provided at the attachment member 244. However, the cylindrical body 246 may be provided at one of the movable member 242 and the attachment member 244, and the ring-shaped body 252 may be provided at the other one.

In the above-described embodiments, the wire 126 is an example of a drive member of the erecting operation mechanism 120 as illustrated in FIGS. 9 and 10. However, a link mechanism may be employed instead of the wire 126.

Figure 30:
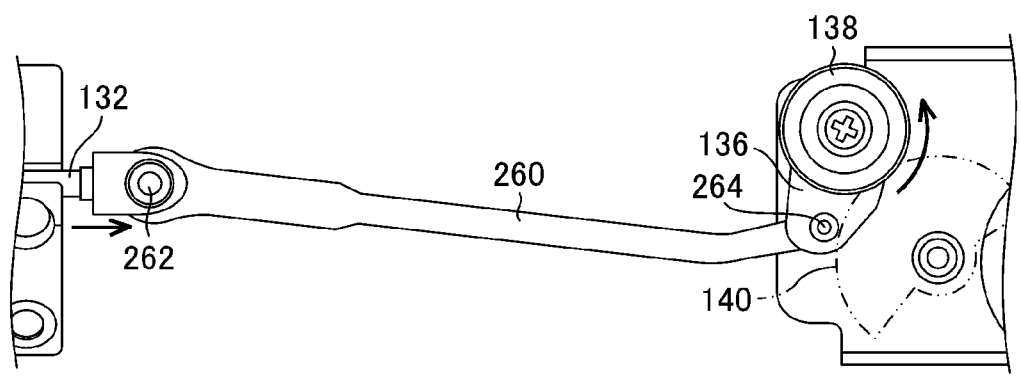
FIG. 30 illustrates a main-part structure in which a first slider and a lever are coupled to each other by using a link sheet metal serving as a link mechanism.
Figure 31:
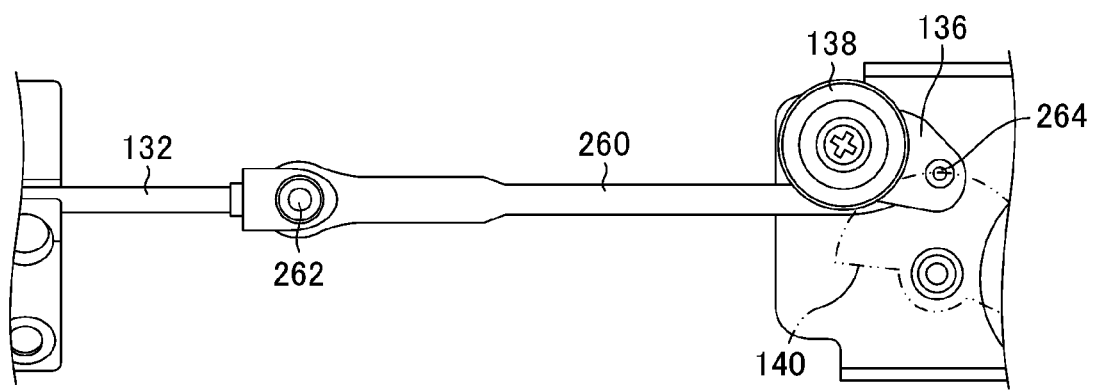
FIG. 31 is a movement explanatory diagram of the link mechanism in FIG. 30.

FIG. 30 illustrates a main-part structure in which a first slider 132 and a lever 136 are coupled to each other by using a link sheet metal 260 serving as a link mechanism. FIG. 31 is a movement explanatory diagram of the link mechanism in FIG. 30.

As illustrated in FIGS. 30 and 31, the distal end of the link sheet metal 260 is rotatably coupled to the proximal end of the first slider 132 via a pin 262, and the proximal end of the link sheet metal 260 is rotatably coupled to the lever 136 via a pin 264.

Accordingly, when the erecting operation lever 20 illustrated in FIGS. 9 and 10 is rotated, a straight advancement motion of the first slider 132 can be transmitted to the lever 136 via the link sheet metal 260 serving as the link mechanism. Thus, the lever 136 is rotated in a rotation range from FIG. 30 to FIG. 31. The resultant rotational force can be transmitted to, for example, the movable member 96 illustrated in FIGS. 9 and 10.

In the above-described embodiments, a duodenum endoscope is described as an example of the endoscope 10. However, the present invention can be applied to any one of various endoscopes, such as an ultrasonic endoscope, as long as the endoscope includes an erecting base that adjusts a lead-out direction of a treatment tool, at a distal end part of an insertion section.

REFERENCE SIGNS LIST 10 endoscope
12 endoscope system
14 processor device
16 light source device
18 display
20 erecting operation lever
22 operation section
22A one side surface
22B the other side surface
24 insertion section
26 distal end part
28 distal end member
28A peripheral surface
30 erecting base
30A guide surface
30B base portion
32 operation section main body
34 holding part
36 extension part
38 break prevention pipe
38A proximal end portion
40 flange
42 treatment tool lead-in port
44 mount portion
44A distal end portion
46 universal cord
48 electric connector
50 light source connector
52 bending part
54 soft part
56 treatment tool
56A distal end portion
58 treatment tool channel
60 wire
62 wire channel
64 angle knob
66 air/water supply button
68 suction button
70 air/water supply nozzle
72 treatment tool lead-out port
74 lead-out port
76 cap
76A opening window
78 partition wall
78A bearing portion
80 partition wall
80A bearing portion
82 erecting base housing chamber
84 rotation shaft
86 rotation shaft
88 optical system housing chamber 90 illumination window
92 observation window
94 lead-in port
95 valve body
96 movable member
98 attachment member
98A attachment member
100 engagement member
102 housing groove
104 opening
106 engagement guide portion
108 engagement guide path
110 deformation generation portion
112 groove
114 groove
116 detachment guide surface
120 erecting operation mechanism
124 first conversion mechanism
126 wire
128 second conversion mechanism
130 crank member
132 first slider
134 second slider
136 lever
138 first gear
140 second gear
142 third gear
144 fourth gear
146 bracket
148 shaft
150 shaft
152 drive shaft
160 beam portion
160A back surface
162 leg portion
164 leg portion
166 O-ring
168 driven shaft
170 coupling structure
170A coupling structure
172 wire assembly
174 engagement hole
174A engagement hole
175 edge portion
176 engagement portion
176A engagement portion
177 tubular portion
178 core portion
180 hole portion
182 cut portion
184 elastic deformation portion
184A slotted portion
186 claw portion
186A claw portion
187 tapered portion
200 branch pipe
202 distal end pipe
204 pipe line
206 pipe line
208 suction pipe
210 coupling structure
212 attachment member
214 engagement hole
216 engagement portion
218 pinch portion
220 shaft portion
222 hole portion
224 small width portion
226 large width portion
228 large diameter portion
230 frictional resistance portion
232 coupling structure
234 attachment member
236 engagement portion
237 slotting groove
238 large diameter portion
240 coupling structure
242 movable member
244 attachment member
246 cylindrical body
248 groove
250 groove
252 ring-shaped body
253 slit
254 pin
256 pin

What is claimed is:

1. An endoscope comprising:
an operation section having an operation section main body provided with an operating member, a holding part connected to the operation section main body and provided with a treatment tool lead-in port, and an extension part extending from the holding part toward a distal end side and provided on a distal end side of the treatment tool lead-in port;
an insertion section that is provided on a distal end side of the extension part and that is inserted into a subject;
a treatment tool erecting base provided at a distal end part of the insertion section;
a movable member that is provided at the extension part and that moves in association with an operation of the operating member;
an erecting operation wire that is coupled to the treatment tool erecting base at a distal end side thereof, that is coupled to the movable member at a proximal end side thereof, and that is pushed/pulled in accordance with a movement of the movable member to move the treatment tool erecting base; and
an attachment member that is provided at a proximal end of the erecting operation wire and that is engaged with the movable member in an attachable/detachable manner by a one-touch operation.

2. The endoscope according to claim 1,
wherein the movable member is arranged to be exposed to outside of the extension part.

3. The endoscope according to claim 2, comprising:
a proximal end opening provided in the extension part;
a distal end opening provided in the distal end part; and
an erecting operation wire channel that is provided in the insertion section and that causes the proximal end opening to communicate with the distal end opening,
wherein the erecting operation wire is inserted through the erecting operation wire channel, has the distal end side that is arranged outside the distal end opening and that is coupled to the treatment tool erecting base, and has the proximal end side that is arranged outside the proximal end opening and that is coupled to the movable member.

4. The endoscope according to claim 2,
wherein an engagement hole is provided in one of the movable member and the attachment member, and an engagement portion that is engaged with the engagement hole in an attachable/detachable manner is provided at the other one.

5. The endoscope according to claim 4,
wherein the engagement portion is provided with an elastic deformation portion that is elastically deformed and engaged with the engagement hole.

6. The endoscope according to claim 5,
wherein a pair of claw portions are formed at the elastic deformation portion, the pair of claw portions being elastically deformable and configured to be latched to an edge portion of the engagement hole, the pair of claw portions being displaced in directions to move toward each other by elastic deformation when the engagement portion is engaged with or disengaged from the engagement hole.

7. The endoscope according to claim 4,
wherein the engagement hole has a small width portion having a first width, and a large width portion having a second width that is larger than the first width, and
wherein the engagement portion has a shaft portion having an outside diameter that is equal to or smaller than the first width, and a fall prevention portion that is provided at a distal end of the shaft portion, that has an outside diameter larger than the first width and smaller than the second width, and that restricts detachment of the shaft portion from the small width portion.

8. The endoscope according to claim 2,
wherein one of the movable member and the attachment member is provided with a cylindrical body extending in a direction perpendicular to an axial direction of the erecting operation wire, and the other one is provided with a ring-shaped body that is rotatably engaged with an outer periphery of the cylindrical body, and
wherein the endoscope comprises a rotation restriction stopper that restricts relative rotations of the cylindrical body and the ring-shaped body.

9. The endoscope according to claim 1, comprising:
an engagement member provided at a distal end of the erecting operation wire; and
a housing groove that is provided in the treatment tool erecting base and that is engaged with the engagement member in an engageable/disengageable manner.

10. The endoscope according to claim 1,
wherein the movable member is rotatably provided while a direction perpendicular to an axial direction of the erecting operation wire serves as a rotation axis.

11. The endoscope according to claim 10,
wherein the operating member is an operating member rotatably supported by the operation section, and
wherein the endoscope comprises
a first conversion mechanism that converts a rotational motion of the operating member into a linear motion,
a drive member that is linearly driven by the first conversion mechanism, and
a second conversion mechanism that converts a linear motion of the drive member into a rotational motion to rotate the movable member.

12. The endoscope according to claim 11,
wherein the second conversion mechanism includes a speed reduction mechanism.

13. The endoscope according to claim 1,
wherein the movable member is formed in a U-like shape.

* * * * *